US 7,029,449 B2

(12) United States Patent
Ogura

(10) Patent No.: US 7,029,449 B2
(45) Date of Patent: Apr. 18, 2006

(54) ARTERIOSCLEROSIS INSPECTING APPARATUS

(75) Inventor: Toshihiko Ogura, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 503 days.

(21) Appl. No.: 10/356,602

(22) Filed: Feb. 3, 2003

(65) Prior Publication Data

US 2003/0167014 A1 Sep. 4, 2003

(30) Foreign Application Priority Data

Mar. 1, 2002 (JP) ............................. 2002-056197

(51) Int. Cl.
*A61B 5/00* (2006.01)
(52) U.S. Cl. ...................... 600/500; 600/485
(58) Field of Classification Search ............... None
See application file for complete search history.

(56) References Cited

U.S. PATENT DOCUMENTS

| 6,440,079 | B1* | 8/2002 | Ogura et al. ............... 600/492 |
| 2002/0091328 | A1* | 7/2002 | Ogura ........................... 600/494 |
| 2003/0139675 | A1* | 7/2003 | Ogura et al. ............... 600/492 |

FOREIGN PATENT DOCUMENTS

| CA | 1088635 | 10/1980 |
| DE | 198 18 147 C1 | 11/1999 |
| JP | A 2001-190506 | 7/2001 |
| JP | A 2001-190509 | 7/2001 |
| WO | WO 90/11043 | 10/1990 |

OTHER PUBLICATIONS

Jungmann et al, "Diagnostic value of the systolic part of the arterial pulse curve, registered using a bloodless technic!" Zeitschrift Fur Kardiologie. West Germany, Jan. 1976 vol. 65, No. 1, pp. 81-88.

(Continued)

*Primary Examiner*—Robert L. Nasser
(74) *Attorney, Agent, or Firm*—Oliff & Berridge, PLC

(57) ABSTRACT

An arteriosclerosis inspecting apparatus including an information obtaining device which obtains information that is related to a velocity at which a pulse wave propagates in a living subject, a blood-pressure measuring device which measures a blood pressure of the subject, a heart-rate measuring device which measures a heart rate of the subject, a pre-ejection-period measuring device which measures a pre-ejection period from a time of starting of contraction of the heart of the subject to a time of starting of ejection of blood from the heart, an ejection-time measuring device which measures an ejection time from the time of starting of ejection of blood from the heart to a time of ending of ejection of blood from the heart, and an arteriosclerosis-inspection-related-augmentation-index determining means for determining an arteriosclerosis-inspection-related augmentation index of the subject, based on the obtained pulse-wave-velocity-related information, the measured blood pressure, the measured heart rate, the measured pre-ejection period, and the measured ejection time, according to a predetermined relationship between (A) (a1) pulse-wave-velocity-related information, (a2) blood pressure, (a3) heart rate, (a4) pre-ejection period and (a5) ejection time, and (B) arteriosclerosis-inspection-related augmentation index.

10 Claims, 17 Drawing Sheets

OTHER PUBLICATIONS

Wang et al., "Reduction of cardiac functional reserve and elevation of aortic stiffness in hyperlipidemic Yucatan minipigs With systemic and coronary atherosclerosis" Vascular Pharmacology, Vo. 39, No. 1-2, Jul. 20, 2002, pp. 69-76.

Brooks et al., "Augmentation of central arterial pressure in type 1 diabetes." Diabetes Care, United States, Oct. 1999, vol. 22, No. 10, pp. 1722-1727.

* cited by examiner

FIG. 3
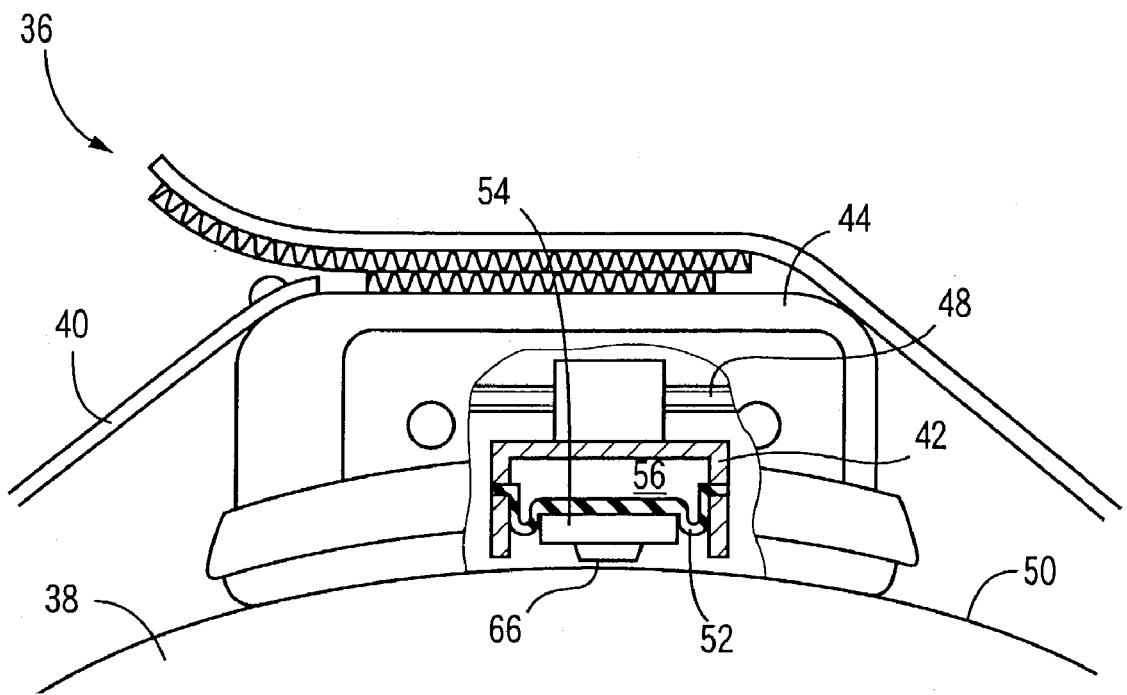

ARTERIOSCLEROSIS INSPECTING APPARATUS

BACKGROUND OF THE INVENTION

1. Field of the Invention

The present invention relates to an arteriosclerosis inspecting apparatus for inspecting arteriosclerosis of a living subject based on an augmentation index or pulse-wave-velocity-related information.

2. Related Art Statement

A degree of arteriosclerosis of a living subject can be evaluated based on augmentation index AI or pulse-wave velocity PWV each as a parameter that is related to artery's degree of elasticity or dilation.

A pulse wave that propagates through an artery of the subject is reflected at a bifurcated or tapered portion of the artery. Therefore, a shape or form of the pulse wave detected from the artery is defined by the composition of an incident-wave component that is produced when blood is ejected from the heart of the subject and advances toward a peripheral portion of the subject, and a reflected-wave component that is produced when the incident-wave component is reflected. Thus, augmentation index AI is obtained by determining a proportion of a reflected-wave component of a pulse wave detected from an artery, such as a carotid artery or a brachial artery, to an incident-wave component of the detected pulse wave. As the artery hardens, phase or amplitude of the reflected-wave component changes. Usually, augmentation index AI is calculated as a percentage of a value obtained by dividing a difference between a magnitude of the detected pulse wave at the time of detection of a peak point of the reflected-wave component and a magnitude of the detected pulse wave at the time of detection of a peak point of the incident-wave component, by a pulse pressure of the detected pulse wave.

Pulse-wave velocity PWV is calculated based on a time difference DT between respective pulse waves detected from two portions of the artery of the subject that are located at different distances from the heart of the subject, and a distance difference DL between the respective distances of those portions from the heart. As the artery hardens, the pulse-wave velocity PWV increases. Usually, the pulse-wave velocity PWV is calculated by dividing the distance difference DL by the time difference DT.

Meanwhile, the form of pulse wave is influenced by not only arteriosclerosis but also various other factors such as blood pressure. Therefore, augmentation index AI may be influenced by cardiac output or afterload, and accordingly it is difficult to diagnose arteriosclerosis based on this index AI only. Thus, the index AI has been used in only cases where a specialist having experience and knowledge uses it.

In addition, since pulse-wave velocity PWV depends on blood pressure, it cannot be used solely. Thus, respective measured values of augmentation index and pulse-wave velocity are used in combination to diagnose a degree of hardening of artery. However, in the case where pulse-wave velocity PWV lowers because of blood-pressure decrease caused by arteriostenosis, or because of aneurysm, it is possible to make an erroneous diagnosis about arteriosclerosis. In addition, in the case where an antihypertensive agent is administered to a hypertensive patient to lower blood pressure of the patient to a normal range and thereby lower pulse-wave velocity PWV of the patient to below a standard value, it is difficult to judge whether arteriosclerosis of the patient has been really improved.

SUMMARY OF THE INVENTION

It is therefore an object of the present invention to provide an arteriosclerosis inspecting apparatus which assures that arteriosclerosis of a living subject can be diagnosed with high accuracy based on arteriosclerosis-inspection-related augmentation index. It is another object of the present invention to provide an arteriosclerosis inspecting apparatus which assures that arteriosclerosis of a living subject can be diagnosed with high accuracy based on arteriosclerosis-inspection-related pulse-wave-velocity related value.

The above object has been achieved by the present invention. According to a first aspect of the present invention, there is provided an apparatus for inspecting arteriosclerosis of a living subject, comprising a pulse-wave-velocity-related-information obtaining device which obtains pulse-wave-velocity-related information that is related to a velocity at which a pulse wave propagates in the subject; a blood-pressure measuring device which measures a blood pressure of the subject; a heart-rate measuring device which measures a heart rate of the subject; a pre-ejection-period measuring device which measures a pre-ejection period from a time of starting of contraction of the heart of the subject to a time of starting of ejection of blood from the heart; an ejection-time measuring device which measures an ejection time from the time of starting of ejection of blood from the heart to a time of ending of ejection of blood from the heart; and an arteriosclerosis-inspection-related-augmentation-index determining means for determining an arteriosclerosis-inspection-related augmentation index of the subject, based on the pulse-wave-velocity-related information obtained by the pulse-wave-velocity-related-information obtaining device, the blood pressure measured by the blood-pressure measuring device, the heart rate measured by the heart-rate measuring device, the pre-ejection period measured by the pre-ejection-period measuring device, and the ejection time measured by the ejection-time measuring device, according to a predetermined relationship between (A) (a1) pulse-wave-velocity-related information, (a2) blood pressure, (a3) heart rate, (a4) pre-ejection period and (a5) ejection time, and (B) arteriosclerosis-inspection-related augmentation index.

According to this aspect, the arteriosclerosis-inspection-related-augmentation-index determining means determines the arteriosclerosis-inspection-related augmentation index based on the pulse-wave-velocity-related information obtained by the pulse-wave-velocity-related-information obtaining device, the blood pressure measured by the blood-pressure measuring device, the heart rate measured by the heart-rate measuring device, the pre-ejection period measured by the pre-ejection-period measuring device, and the ejection time measured by the ejection-time measuring device, according to the predetermined relationship. Thus, the arteriosclerosis-inspection-related augmentation index is determined based on the pulse-wave-velocity-related information corresponding to the elasticity of blood vessel of the subject, the blood pressure of the subject, the heart rate (i.e., pulse rate) corresponding to the activity of autonomic nerve of the subject, and the pre-ejection period and the ejection time both corresponding to the cardiac (e.g., cardiac-output) function of the subject. Therefore, the arteriosclerosis-inspection-related augmentation index enjoys a high degree of reliability reflecting the condition of circulatory organ of the subject and can be used to make an accurate diagnosis on arteriosclerosis of the subject. Thus, the accuracy of diagnosis of arteriosclerosis is improved.

According to a preferred feature of the first aspect of the present invention, the predetermined relationship is represented by a following expression: $AI_E = a \times PWV + b \times BP + c \times HR + d \times ET + e \times PEP + f$, where PWV is pulse-wave-velocity-related information, BP is blood pressure, HR is heart rate, PEP is pre-ejection period, ET is ejection time, $AI_E$ is arteriosclerosis-inspection-related augmentation index, a, b, c, d, and e are coefficients, and f is a constant.

According to this feature, the coefficients and constant a, b, c, d, e, and f may be determined in advance for each individual living subject, and a degree of arteriosclerosis of the each subject can be accurately inspected or evaluated. It is preferred that a systolic blood pressure SYS be used as the blood pressure BP.

According to another feature of the first aspect of the present invention, the arteriosclerosis inspecting apparatus further comprises a display device which displays the arteriosclerosis-inspection-related augmentation index of the subject determined by the arteriosclerosis-inspection-related-augmentation-index determining means.

According to this feature, an operator such as a doctor can observe the arteriosclerosis-inspection-related augmentation index displayed by the display device and thereby accurately inspect or evaluate the degree of arteriosclerosis of the subject.

According to another feature of the first aspect of the present invention, the predetermined relationship is predetermined for each living subject, and the arteriosclerosis inspecting apparatus further comprises a display device which displays the coefficients a, b, c, d, and e and the constant f of the predetermined relationship.

According to this feature, the operator can observe respective changes of the coefficients and thereby accurately evaluate the therapeutic effect of antihypertensive agent or treatment.

According to a second aspect of the present invention, there is provided an apparatus for inspecting arteriosclerosis of a living subject, comprising an augmentation-index measuring device which measures an augmentation index of the subject that is a proportion of a magnitude of a reflected-wave component of a pulse wave of the subject to a magnitude of an incident-wave component of the pulse wave; a blood-pressure measuring device which measures a blood pressure of the subject; a heart-rate measuring device which measures a heart rate of the subject; a pre-ejection-period measuring device which measures a pre-ejection period from a time of starting of contraction of the heart of the subject to a time of starting of ejection of blood from the heart; an ejection-time measuring device which measures an ejection time from the time of starting of ejection of blood from the heart to a time of ending of ejection of blood from the heart; and an arteriosclerosis-inspection-related-pulse-wave-velocity-related-value determining means for determining an arteriosclerosis-inspection-related pulse-wave-velocity-related value of the subject, based on the augmentation index measured by the augmentation-index measuring device, the blood pressure measured by the blood-pressure measuring device, the heart rate measured by the heart-rate measuring device, the pre-ejection period measured by the pre-ejection-period measuring device, and the ejection time measured by the ejection-time measuring device, according to a predetermined relationship between (A) (a1) augmentation index, (a2) blood pressure, (a3) heart rate, (a4) pre-ejection period and (a5) ejection time, and (B) arteriosclerosis-inspection-related pulse-wave-velocity-related value.

According to this aspect, the arteriosclerosis-inspection-related-pulse-wave-velocity-related-value determining means determines the arteriosclerosis-inspection-related pulse-wave-velocity-related value based on the augmentation index measured by the augmentation-index measuring device, the blood pressure measured by the blood-pressure measuring device, the heart rate measured by the heart-rate measuring device, the pre-ejection period measured by the pre-ejection-period measuring device, and the ejection time measured by the ejection-time measuring device, according to the predetermined relationship. Thus, the arteriosclerosis-inspection-related wave-velocity-related value is determined based on the augmentation index corresponding to the elasticity of blood vessel of the subject, the blood pressure of the subject, the heart rate (i.e., pulse rate) corresponding to the activity of autonomic nerve of the subject, and the pre-ejection period and the ejection time both corresponding to the cardiac (e.g., cardiac-output) function of the subject. Therefore, the arteriosclerosis-inspection-related wave-velocity-related value enjoys a high degree of reliability reflecting the condition of circulatory organ of the subject and can be used to make an accurate diagnosis on arteriosclerosis of the subject. Thus, the accuracy of diagnosis of arteriosclerosis is improved.

According to a preferred feature of the second aspect of the present invention, the predetermined relationship is represented by a following expression: $PWV_E = a' \times AI + b' \times BP + c' \times HR + d' \times ET + e' \times PEP + f'$, where $PWV_E$ is arteriosclerosis-inspection-related pulse-wave-velocity-related value, BP is blood pressure, HR is heart rate, PEP is pre-ejection period ET is ejection time, AI is augmentation index, a', b', c', d', and e' are coefficients, and f' is a constant.

According to this feature, the coefficients and constant a', b', c', d', e', and f' may be determined in advance for each individual living subject, and a degree of arteriosclerosis of the each subject can be accurately inspected or evaluated. It is preferred that a systolic blood pressure SYS be used as the blood pressure BP.

According to another feature of the second aspect of the present invention, the arteriosclerosis inspecting apparatus further comprises a display device which displays the arteriosclerosis-inspection-related pulse-wave-velocity-related value of the subject determined by the arteriosclerosis-inspection-related-pulse-wave-velocity-related-value determining means.

According to this feature, the operator can observe the arteriosclerosis-inspection-related pulse-wave-velocity-related value displayed by the display device and thereby accurately inspect or evaluate the degree of arteriosclerosis of the subject.

According to another feature of the second aspect of the present invention, the predetermined relationship is predetermined for each living subject, and the arteriosclerosis inspecting apparatus further comprises a display device which displays the coefficients a', b', c', d', and e' and the constant f' of the predetermined relationship.

According to this feature, the operator can observe respective changes of the coefficients and thereby accurately evaluate the therapeutic effect of antihypertensive agent or treatment.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 3 is an enlarged view of the pressure-pulse-wave detecting probe of FIG. 2, a portion of the probe being cut away;

DETAILED DESCRIPTION OF PREFERRED EMBODIMENTS

Figure 1:
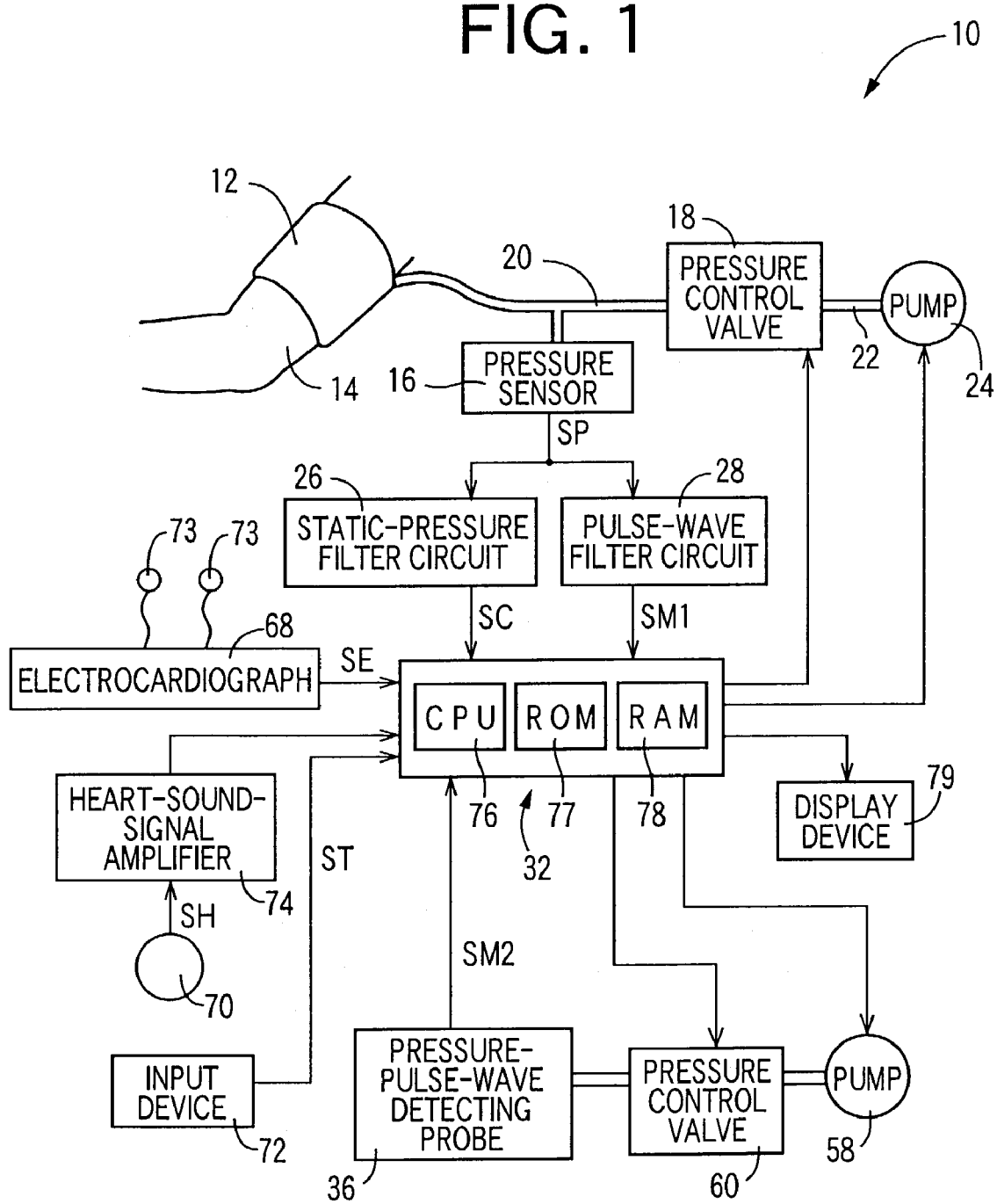
FIG. 1 is a diagrammatic view showing a circuitry of an arteriosclerosis inspecting apparatus to which the present invention is applied.

Hereinafter, there will be described an embodiment of the present invention in detail by reference to the drawings. FIG. 1 is a diagrammatic view showing a circuitry of an arteriosclerosis inspecting apparatus 10 to which the present invention is applied.

In the arteriosclerosis inspecting apparatus 10 shown in FIG. 1, an inflatable cuff 12 includes a belt-like cloth bag and a rubber bag accommodated in the cloth bag, and is adapted to be wound around an upper arm 14 of a patient as a living subject. The cuff 12 is connected via a piping 20 to a pressure sensor 16 and a pressure control valve 18. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal, SP, representing the detected air pressure, to a static-pressure filter circuit 26 and a pulse-wave filter circuit 28. The static-pressure filter circuit 26 includes a low-pass filter that extracts, from the pressure signal SP, a cuff-pressure signal, SC, representing a static component of the detected air pressure, i.e., a pressing pressure of the cuff 12 (hereinafter, referred to as the cuff pressure, PC). The filter circuit 26 supplies the cuff-pressure signal SC to an electronic control device 32 via an A/D (analog-to-digital) converter, not shown. The pulse-wave filter circuit 28 includes a band-pass filter that extracts, from the pressure signal SP, a cuff-pulse-wave signal, SM1, representing an oscillatory component of the detected air pressure that has prescribed frequencies. The filter circuit 28 supplies the cuff-pulse-wave signal SM1 to the control device 32 via an A/D converter, not shown. The oscillatory component represented by the cuff-pulse-wave signal SM1 is a brachial pulse wave, wb, that is, pressure oscillation produced in synchronism with heartbeats of the subject and transmitted to the cuff 12 from a brachial artery of the upper arm 14 being pressed by the cuff 12.

Figure 2:
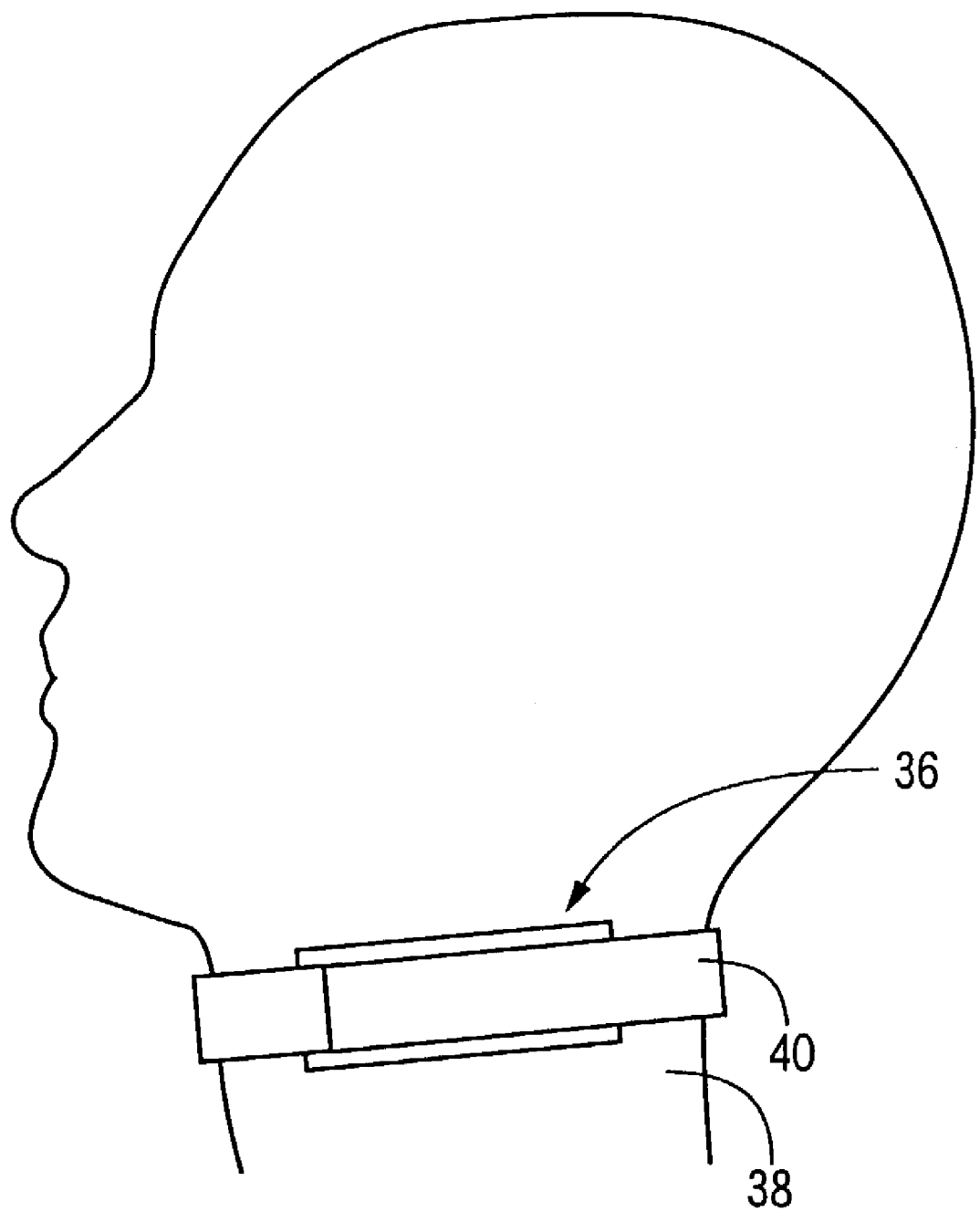
FIG. 2 is an illustrative view showing a state in which a pressure-pulse-wave detecting probe of the apparatus of FIG. 1 is worn on a neck portion of a living subject.

The present arteriosclerosis inspecting apparatus 10 includes a pressure-pulse-wave detecting probe 36, shown in FIG. 2, that functions as a carotid-pulse-wave detecting device. The pressure-pulse-wave detecting probe 36 is worn on a neck portion 38 of the subject, as illustrated in FIG. 2, with the help of a band 40. As shown in detail in FIG. 3, the pressure-pulse-wave detecting probe 36 includes a container-like sensor housing 42; a case 44 which accommodates the sensor housing 42; and a feed screw 48 which is threadedly engaged with the sensor housing 42 and is rotated by an electric motor, not shown, provided in the case 44 so as to move the sensor housing 42 in a widthwise direction of a carotid artery 46. With the help of the band 40, the pressure-pulse-wave detecting probe 36 is detachably attached to the neck portion 38, such that an open end of the sensor housing 42 is opposed to a body surface 50 of the neck portion 38.

In addition, the pressure-pulse-wave detecting probe 36 includes a pressure-pulse-wave sensor 54 which is secured via a diaphragm 52 to an inner wall of the sensor housing 42, such that the sensor 54 is movable relative to the housing 42 and is advanceable out of the open end of the same 42. The sensor housing 42, the diaphragm 52, etc. cooperate with one another to define a pressure chamber 56, which is supplied with a pressurized air from an air pump 58 via a pressure-control valve 60, as shown in FIG. 1, so that the pressure-pulse-wave sensor 54 is pressed against the body surface 50 with a pressing force corresponding to the air pressure in the pressure chamber 56.

The sensor housing 42 and the diaphragm 52 cooperate with each other to provide a pressing device 62 which presses the pressure-pulse-wave sensor 54 against the carotid artery 46, and the feed screw 48 and the not-shown motor cooperate with each other to provide a widthwise-direction moving device 64 which moves the pressure-pulse-wave sensor 54 in the widthwise direction of the carotid artery 46 and thereby changes a pressing position where the sensor 54 is pressed on the body surface 50.

Figure 4:
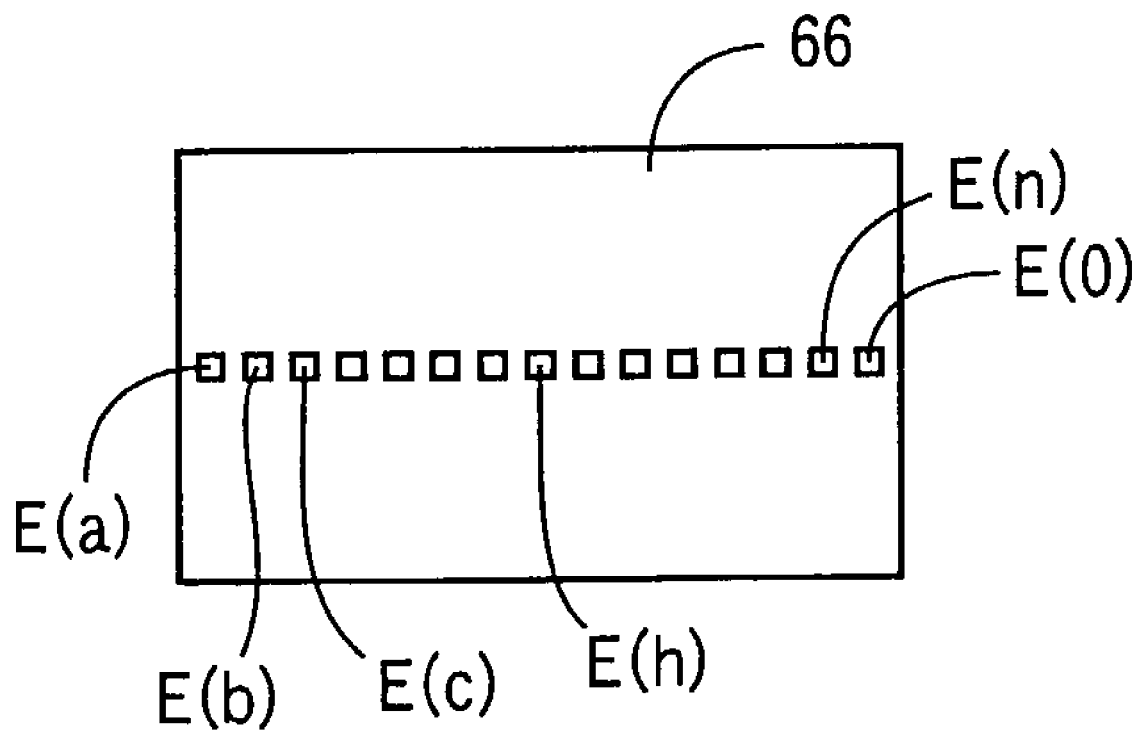
FIG. 4 is a view for explaining a state in which an array of pressure-sensing elements is provided in a press surface of a pressure-pulse-wave sensor shown in FIG. 1.

The pressure-pulse-wave sensor 54 has a pressing surface 66, and a number of semiconductor pressure-sensing elements (hereinafter, referred to as the "pressure-sensing elements") E which are arranged in the pressing surface 66 at a regular interval in the widthwise direction of the carotid artery 46, i.e., in the direction of movement of the sensor 54 parallel to the feed screw 48, over a length greater than the diameter of the carotid artery 46. For example, as shown in FIG. 4, fifteen pressure-sensing elements E(a), E(b), ..., E(o) are arranged at a regular interval of, e.g., 0.6 mm.

Figure 5:
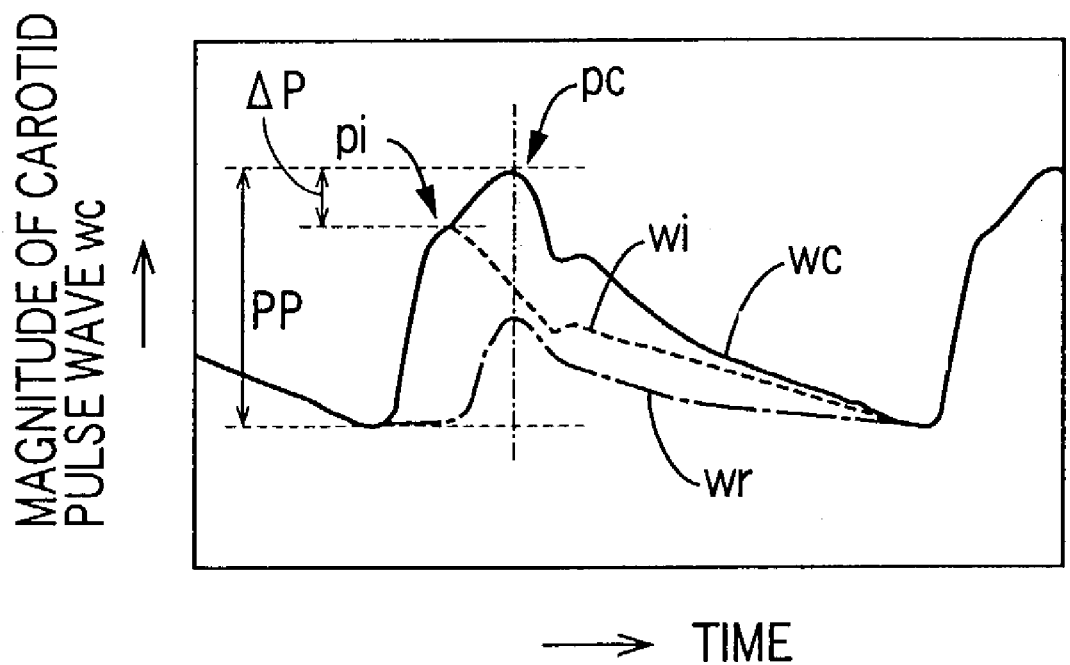
FIG. 5 is a view showing an example of a carotid pulse wave, wc, represented by a pressure-pulse-wave signal, SM2, supplied from one of the pressure-sensing elements of the pressure-pulse-wave sensor of FIG. 1.

The pressure-pulse-wave detecting probe 36, constructed as described above, is pressed against the body surface 50 of the neck portion 38 right above the carotid artery 46, so that the pressure-pulse-wave sensor 54 detects a pressure pulse wave (i.e., a carotid pulse wave, wc) which is produced from the carotid artery 46 and is propagated to the body surface 50, and supplies a pressure-pulse-wave signal SM2 representing the detected carotid pulse wave wc, to the control device 32 via an A/D converter, not shown. An example of the carotid pulse wave wc represented by the pressure-pulse-wave signal SM2 continuously supplied from the pressure-pulse-wave sensor 54 is indicated at solid line in FIG. 5.

Back to FIG. 1, the arteriosclerosis inspecting apparatus 10 further includes an electrocardiograph 68, a heart-sound microphone 70, and an input device 72. The electrocardiograph 68 includes a plurality of electrodes 73 that are attached to a body surface of the subject such that the subject's heart is positioned between the electrodes attached. The electrocardiograph 68 detects, through the electrodes 73, an action potential of the cardiac muscle, and supplies, to the control device 32 via an A/D converter, not shown, an electrocardiogram signal, SE, representing the detected action potential.

The heart-sound microphone 70 is attached, with an adhesive tape or the like, not shown, to a chest of the subject, not shown. The microphone 70 incorporates a piezoelectric element, not shown, which converts heart sounds produced from the subject's heart, into an electric signal, i.e., a heart-sound signal SH. A heart-sound-signal amplifier 74 includes four sorts of filters, not shown, which cooperate with one another to amplify a high-pitch component having a small energy and attenuate a low-pitch component having a great energy, and amplifies and filters the heart-sound signal SH supplied from the microphone 70. The heart-sound signal SH amplified and filtered by the amplifier 74 is supplied to the control device 32 via an A/D converter, not shown.

An input device 72 includes a plurality of keys, not shown, which are operated by an operator such as a doctor or a nurse to input a stature, T, of the subject. The input device 72 supplies a stature signal ST representing the inputted subject's stature T, to the control device 32.

The control device 32 is provided by a so-called microcomputer including a CPU (central processing unit) 76, a ROM (read only memory) 77, a RAM (random access memory) 78, and an I/O (input-and-output) port, not shown. The CPU 76 processes signals according to the control programs pre-stored in the ROM 77 by utilizing the temporary-storage function of the RAM 78, and supplies drive signals via the I/O port to the air pumps 24, 58 and the pressure control valves 18, 60 so as to control the cuff pressure PC and the pressure in the pressure chamber 56. Moreover, the CPU 76 obtains and determines, based on the cuff-pulse-wave signal SM1, the pressure-pulse-wave signal SM2, the cuff-pressure signal SC, the electrocardiogram signal SE, the heart-sound signal SH, and the stature signal ST, each supplied to the control device 32, a piece of waveform-related information, such as a blood-pressure value BP, and an augmentation index AI, and operates a display device 79 to display the thus obtained information and index.

Figure 6:
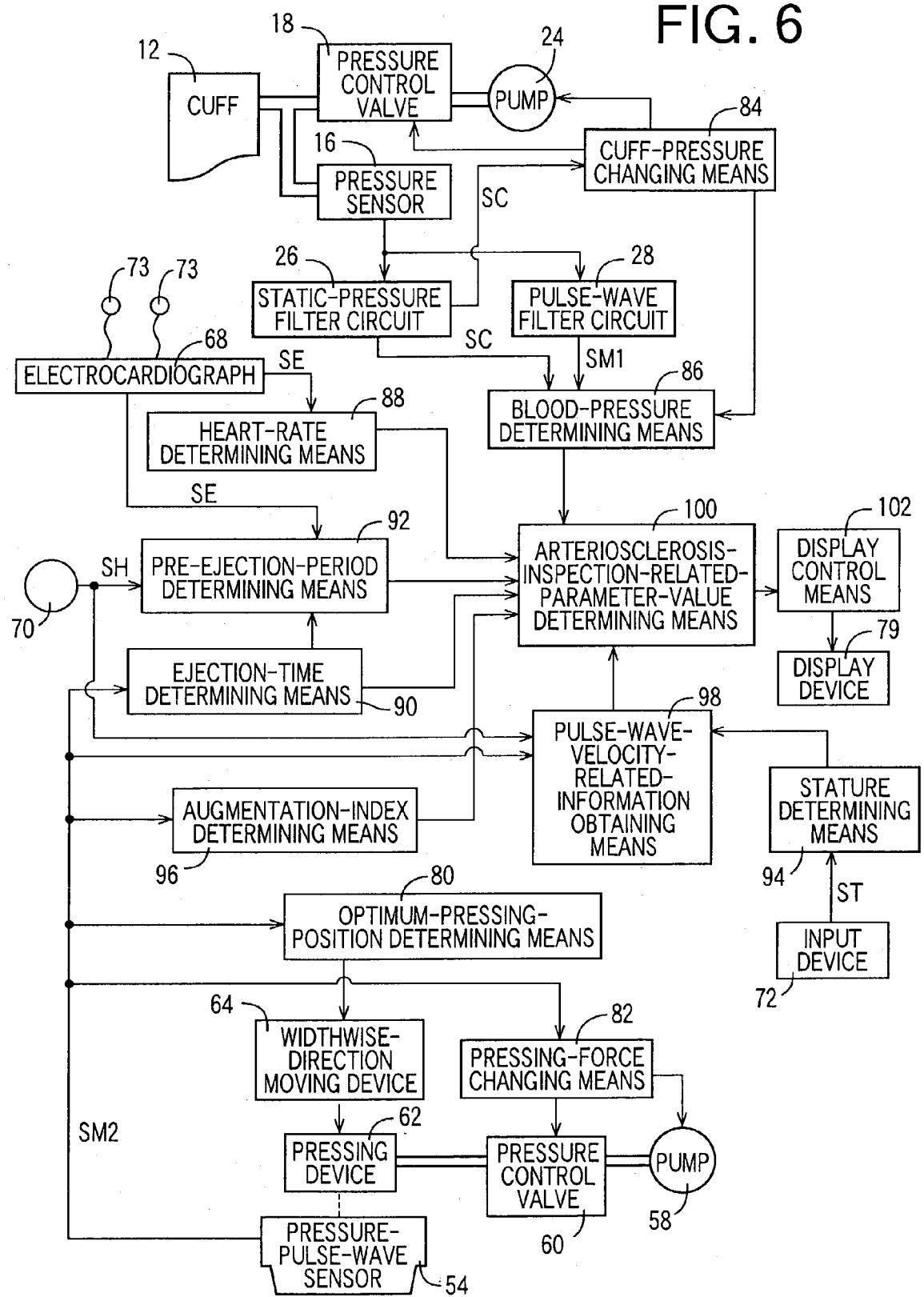
FIG. 6 is a block diagram for explaining essential control functions of an electronic control device of the apparatus of FIG. 1.

FIG. 6 is a block diagram for explaining the essential control functions of the control device 32 of the arteriosclerosis inspecting apparatus 10.

An optimum-pressing-position determining means 80 judges whether a prescribed pressing-position changing condition is satisfied, i.e., whether one (hereinafter, referred to as the "highest-pressure detecting element EM") of the pressure-sensing elements E of the pressure-pulse-wave sensor 54 that detects the highest pressure of the respective pressures detected by all the elements E is positioned in one of prescribed opposite end portions of the array of pressure-sensing elements E. Each of the prescribed opposite end portions of the array of elements E may be a range having a prescribed length including a corresponding one of the opposite ends of the array of elements E, or a range accommodating a prescribed number of elements E including a corresponding one of the respective elements E located at the opposite ends of the array. The highest-pressure detecting element EM is one of the elements E that is positioned right above the carotid artery 46. When this pressing-position changing condition is satisfied, the optimum-pressing-position determining means 80 carries out the following pressing-position changing operation: After the pressing device 62 once moves the pressure-pulse-wave sensor 54 away from the body surface 50, the widthwise-direction moving device 64 moves the pressing device 62 and the sensor 54 over a prescribed distance, and then the pressing device 62 again presses the sensor 54 with a prescribed, considerably low first pressing force HDP1 that is smaller than an optimum pressing force HDPO, described later. In this state, the determining means 80 judges again whether the prescribed pressing-position changing condition is satisfied. The determining means 80 repeats carrying out the above-described operation and judgment till the pressing-position changing condition is not satisfied any longer, preferably till the highest-pressure detecting element EM is positioned in a prescribed middle portion of the array of elements E. The length, or element number, employed for each of the opposite end portions of the array of elements E is prescribed based on the diameter of the artery (i.e., the carotid artery 46) to be pressed by the pressure-pulse-wave sensor 54, and may be one fourth of the diameter.

A pressing-force changing means 82 changes, after the optimum-pressing-position determining means 80 positions the pressure-pulse-wave sensor 54 at the optimum pressing position, a pressing force HDP (i.e., a hold-down pressure) applied by the pressing device 62 to the sensor 54, within a prescribed pressing-force range, either stepwise in response to each heartbeat of the subject or continuously at a prescribed, considerably low rate. Based on the carotid pulse wave wc obtained during the changing of the pressing force HDP, the changing means 82 determines an optimum pressing force HDPO and maintains the pressing force applied by the pressing device 62 to the sensor 54, at the thus determined optimum pressing force HDPO. Here, the optimum pressing force HDPO is so determined that a pulse pressure PP of the carotid pulse wave wc detected by the highest-pressure detecting element EM pressed by the pressing force HDP (i.e., a difference obtained by subtracting the smallest magnitude, from the greatest magnitude, of one heartbeat-synchronous pulse of the carotid pulse wave wc) may not be smaller than a predetermined lower-limit pulse pressure $PP_L$. The lower-limit pulse pressure $PP_L$ is experimentally predetermined as a value which assures that a clear carotid pulse wave wc can be detected. If the pulse pressure PP is too small, a clear carotid pulse wave wc cannot be obtained.

A cuff-pressure changing means 84 operates, based on the cuff-pressure signal SC supplied from the static-pressure filter circuit 26, the pressure control valve 18 and the air pump 24 so as to quickly increase the cuff pressure PC to a prescribed increase-target pressure (e.g., 180 mmHg) that would be higher than a systolic blood pressure $BP_{SYS}$ of the patient and, subsequently, slowly decrease the cuff pressure at a rate of, e.g., 2 or 3 mmHg/sec. After a blood-pressure determining means 86, described below, determines blood-pressure values BP of the patient, the changing means 84 releases the cuff pressure to an atmospheric pressure.

The blood-pressure determining means 86 determines, based on the cuff-pressure signal SC continuously supplied from the static-pressure filter circuit 26, and the cuff-pulse-wave signal SM1 continuously supplied from the pulse-wave filter circuit 28, each during the slow decreasing of the cuff pressure PC under the control of the cuff-pressure changing means 84, a systolic blood pressure $BP_{SYS}$(=SYS), a mean blood pressure $BP_{MEAN}$, and a diastolic blood pressure $BP_{DIA}$ of the patient, according to well-known oscillometric blood-pressure determining algorithm. The thus determined systolic blood pressure $BP_{SYS}$ corresponds to a peak point (i.e., a maximal magnitude) of each of successive heartbeat-synchronous pulses of the brachial pulse wave wb. Therefore, as systolic blood pressure $BP_{SYS}$ increases, magnitude of peak point of each heartbeat-synchronous pulse of brachial pulse wave wb also increases. In addition, as magnitude of peak point of each heartbeat-synchronous pulse of brachial pulse wave wb changes, magnitude of peak point pc of each heartbeat-synchronous pulse of carotid pulse wave wc also changes. Thus, as systolic blood pressure $BP_{SYS}$ changes, magnitude of peak point pc of each heartbeat-synchronous pulse of carotid pulse wave wc also changes, and accordingly waveform of each heartbeat-synchronous pulse of carotid pulse wave wc also changes. Therefore, systolic blood pressure $BP_{SYS}$ c is a sort of waveform-related information that is related to waveform of a pulse wave. The blood-pressure determining means 86 also functions as part of a blood-pressure measuring device.

A heart-rate determining means 88 iteratively, e.g., upon each heartbeat of the subject, determines, as a pulse period, RR (sec), a time interval between respective prescribed periodic portions (e.g., respective R-waves) of each pair of successive heartbeat-synchronous pulses of the electrocardiographic pulse wave (i.e., electrocardiogram) represented by the electrocardiogram signal SE continuously supplied from the electrocardiograph 68, and determines a heart rate, HR, (/minute) by multiplying the inverse (i.e., 1/RR) of the pulse period RR by 60. Change of heart rate HR indicates change of time interval between respective rising points of each pair of successive heartbeat-synchronous pulses of pulse wave. Therefore, as heart rate HR changes, waveform of pulse wave also changes. Thus, heart rate HR is a sort of waveform-related information. The heart-rate determining means 88 functions as part of a heart-rate measuring device.

Figure 7:
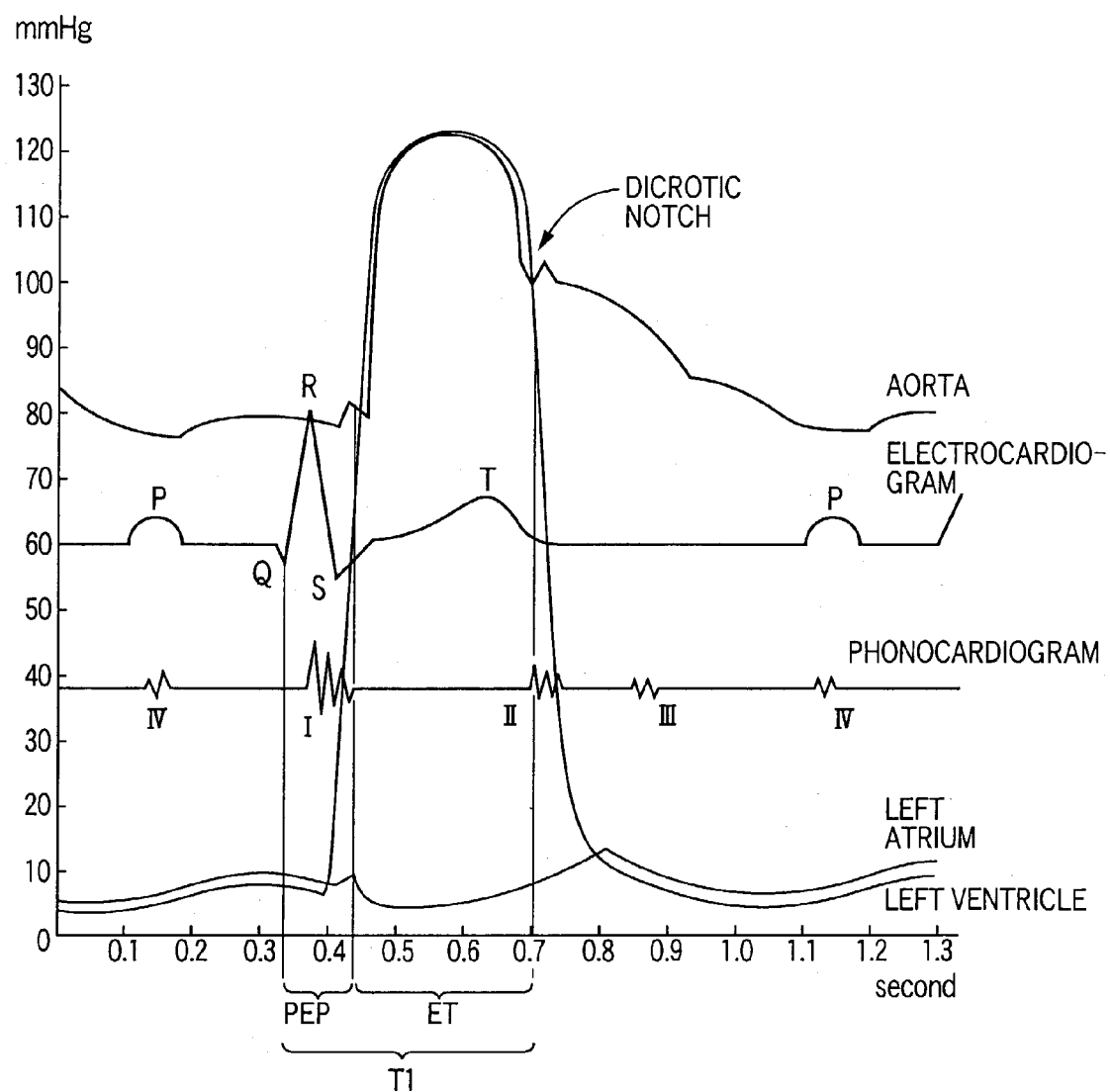
FIG. 7 is a schematic view showing pressure in aorta, pressure in left atrium, pressure in left ventricle, electrocardiogram, and phonocardiogram along a common time axis.

An ejection-time determining means 90 iteratively, e.g., upon each heartbeat of the subject, and non-invasively determines an ejection time, ET, (msec) in which aortic valve is opened and blood is ejected from left ventricle of the subject. FIG. 7 schematically shows pressure in aorta, pressure in left atrium, pressure in left ventricle, electrocardiogram, and electro-phonogram along a common time axis. As shown in FIG. 7, a time difference between rising point, and dicrotic notch, of aortic pulse wave can be determined as ejection time ET. Meanwhile, since waveform of carotid pulse wave wc is similar to waveform of aortic pulse wave, carotid pulse wave wc can be used in place of aortic pulse wave. Thus, a time difference between rising point, and dicrotic notch, of carotid pulse wave wc continuously detected by the pressure-pulse-wave sensor 54 is determined as ejection time ET. Ejection time ET is a magnitude of an incident-wave component of a pulse wave as seen in a direction parallel to the time axis. Therefore, as ejection time ET changes, waveform of the pulse wave also changes. Thus, ejection time ET is a sort of waveform-related information. The ejection-time determining means 90 functions as part of an ejection-time measuring device.

A pre-ejection-period determining means 92 iteratively, e.g., upon each heartbeat of the subject, and non-invasively determines a pre-ejection period, PEP, (msec), i.e., a time period between start point of systolic time of the heart and opening of aortic valve, i.e., starting of ejection of blood. For example, first, the pre-ejection-period determining means 92 determines a time, T1, between a time when the electrocardiograph 68 detects a wave (e.g., R-wave) indicative of excitation of ventricular muscle, and a time when the heart-sound microphone 70 detects a start point of a second heart sound II. Second heart sound II corresponds to closing of aortic valve. As shown in FIG. 7, the thus determined time T1 is equal to a sum of pre-ejection period PEP and ejection time ET. Therefore, the pre-ejection-period determining means 92 determines the pre-ejection period PEP by subtracting, from the time T1, the ejection time ET determined by the ejection-time determining means 90. Since pre-ejection period PEP is a time period from starting of contraction of cardiac muscle of left ventricle to starting of ejection of blood, it is also called isovolumetric contraction time. As pre-ejection period PEP increases, pressure at the time of starting of ejection of blood also increases, and accordingly the ejection time decreases. Thus, as pre-ejection period PEP changes, waveform of pulse wave also changes. Therefore, pre-ejection period PEP is a sort of waveform-related information. The pre-ejection-period determining means 92 functions as part of a pre-ejection-period measuring device.

A stature determining means 94 determines, based on the stature signal ST supplied from the input device 72, a stature T of the subject. A pulse wave is composed of an incident-wave component and a reflected-wave component, as described previously, and it is speculated that the reflected wave is mainly produced at a bifurcated portion of a common iliac artery. As stature T varies, distance between the position where the pulse wave is detected and the bifurcated portion of common iliac artery also varies and accordingly time needed for the reflected wave to reach the position where the pulse wave is detected also varies. Therefore, as stature T varies, amount of overlapping of the incident-wave and reflected-wave components also varies. Thus, stature T is a sort of waveform-related information, and the stature determining means 94 functions as a sort of waveform-related-information obtaining means. In addition, as stature T changes, distance DL between the heart and carotid artery also varies, and accordingly pulse-wave velocity PWV that is determined based on distance DL and pulse-wave propagation time difference DT also varies. Therefore, distance DL and pulse-wave propagation time difference DT are corrected using stature T so as to obtain accurate pulse-wave velocity PWV.

An augmentation-index determining means 96 determines, first, respective times of occurrence of respective peak points, pi and pr, of incident-wave and reflected-wave components, wi and wr, which are contained in a heartbeat-synchronous pulse of the carotid pulse wave wc continuously detected by the highest-pressure detecting element EM of the pressure-pulse-wave sensor 54 in the state in which the pressing force HDP applied to the sensor 54 is maintained at the optimum pressing force HDPO. Then, the augmentation-index determining means 96 iteratively, e.g., upon each heartbeat of the subject determines a pressure difference ΔP by subtracting a magnitude of the carotid pulse wave wc at the time of occurrence of peak point pi of incident-wave component wi from a magnitude of the carotid pulse wave wc at the time of occurrence of peak point pr of reflected-wave component wr, and additionally determines a pulse pressure PP by subtracting the smallest magnitude of the heartbeat-synchronous pulse of the carotid pulse wave wc from the greatest magnitude of the same. Moreover, the determining means 96 substitutes the pressure difference ΔP and the pulse pressure PP for the following Expression 1, so as to determine an augmentation index AI (%):

$$AI=(\Delta P/PP)\times 100(\%) \tag{1}$$

Here, the manner in which the time of occurrence of peak point pi of incident-wave component wi of the carotid pulse wave wc is determined is described. The carotid pulse wave wc contains the incident-wave component wi, indicated at broken line in FIG. 5, and the peak point pi of the incident-wave component wi corresponds to an inflection point or a maximal point of the composite carotid pulse wave (i.e., observed pulse wave) wc that occurs between a rising point and a peak point pc of the composite pulse wave wc. In the example shown in FIG. 5, the peak point pi of the incident wave wi corresponds to an inflection point of the observed pulse wave wc. To this end, the continuously obtained pressure-pulse-wave signal SM2 is subjected to a common treatment to detect an inflection point or a maximal point. Here, the common treatment may be a differentiation treatment or a filter treatment.

Generally, the time of occurrence of the peak point of the reflected wave wr is a time of occurrence of the first maximal point following the peak point pi of the incident wave wi. Therefore, in the case, shown in FIG. 5, where a peak point pi of an incident wave wi does not coincide with a peak point pc of a carotid pulse wave wc, a time of occurrence of peak point pc of the carotid pulse wave wc is determined as a time of occurrence of a peak point of a reflected wave wr. On the other hand, in the case where a peak point pi of an incident wave wi is so large that the peak point pi of the incident wave wi also defines a peak point of a carotid pulse wave wc, a time of occurrence of the first maximal point following the peak point pi of the incident wave wi is determined as a time of occurrence of a peak point of a reflected wave wr.

A pulse-wave-velocity-related-information obtaining means 98 non-invasively obtains a velocity PWV (unit: m/sec) at which a pressure pulse wave produced from the heart of the subject propagates through an artery of the subject. For example, the obtaining means 98 determines a propagation time DT, i.e., a delay time from a second heart sound II, detected by the heart-sound microphone 70, that indicates closing of the aortic valve, to a dicrotic notch of the carotid pulse wave detected by the pressure-pulse-wave sensor 54, and determines a pulse-wave velocity PWV (=DL/DT) by dividing, by the propagation time DT, a pre-set distance DL that has been corrected by the subject's stature T.

An arteriosclerosis-inspection-related-parameter-value determining means 100 determines an arteriosclerosis-inspection-related augmentation index $AI_E$ of the subject based on the pulse-wave-velocity-related information, e.g. pulse-wave velocity PWV, obtained by the pulse-wave-velocity-related-information obtaining means 98, the blood pressure, e.g., systolic blood pressure SYS determined by the blood-pressure determining means 86, the heart rate HR determined by the heart-rate determining means 88, the pre-ejection period PWP determined by the pre-ejection-period determining means 92, and the ejection time determined by the ejection-time determining means 90, according to the following Expression 2, and additionally determines an arteriosclerosis-inspection-related pulse-wave-velocity-related value, e.g., pulse-wave velocity $PWV_E$, of the subject, based on the augmentation index AI determined by the augmentation-index determining means 96, the blood pressure, e.g., systolic blood pressure SYS, determined by the blood-pressure determining means 86, the heart rate HR determined by the heart-rate determining means 88, the pre-ejection period PEP determined by the pre-ejection-period determining means 92, and the ejection time determined by the ejection-time determining means 90, according to the following Expression 3:

$$AI_E = a \times PWV + b \times SYS + c \times HR + d \times ET + e \times PEP + f \tag{2}$$

where PWV is pulse-wave velocity, SYS is systolic blood pressure, HR is heart rate, PEP is pre-ejection period, ET is ejection time, a, b, c, d, and e are coefficients, and f is a constant.

$$PWV_E = a' \times AI + b' \times SYS + c' \times HR + d' \times ET + e' \times PEP + f' \tag{3}$$

where AI is augmentation index, SYS is systolic blood pressure, HR is heart rate, PEP is pre-ejection period, ET is ejection time, a', b', c', d', and e' are coefficients, and f' is a constant.

A display control means 102 operates the display device 79 to display the arteriosclerosis-inspection-related augmentation index $AI_E$ and/or the arteriosclerosis-inspection-related pulse-wave velocity $PWV_E$, each determined by the arteriosclerosis-inspection-related-parameter-value determining means 100, in such a manner that the index $AI_E$ and/or the velocity PWVE are/is indicated in digital values such as numerals or in analog values such as bar graphs, so that the operator can easily make a diagnosis based on the indicated index and/or velocity. Simultaneously, the display control means 102 operates the display device 79 to display Expression 2 and/or Expression 3, and the coefficients a, b, c, d, and e and the constant f of Expression 2 and/or the coefficients a', b', c', d', and e' and the constant f' of Expression 3. In addition, if the control device 32 has determined and stored, for the same subject, one or more past arteriosclerosis-inspection-related augmentation index values $AI_E$ and/or one or more past arteriosclerosis-inspection-related pulse-wave velocity values $PWV_E$, and one or more past sets of coefficients and constant of Expression 2 and/or Expression 3, then the display control means 102 operates the display device 79 to display respective data points of each of those parameters along a time axis, or respective differences of the respective data points of each parameter from their previous data points, so that the operator can easily observe respective time-wise changes of those parameters.

Figure 8:
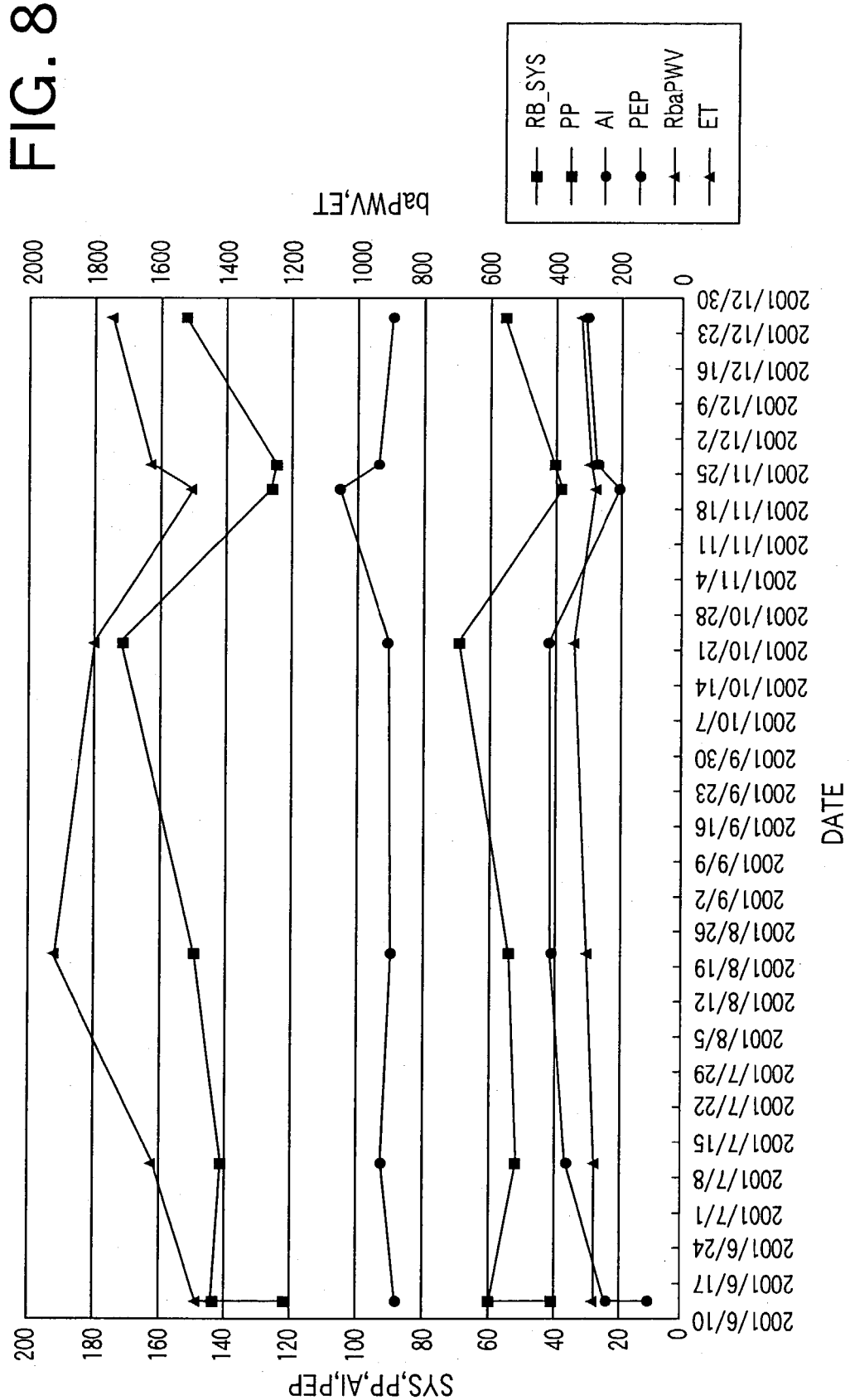
FIG. 8 is a graph showing respective timewise changes of a plurality of physical parameters that are non-invasively obtained in half a year from a male person in his sixties who has been treated against hypertension.
Figure 9:
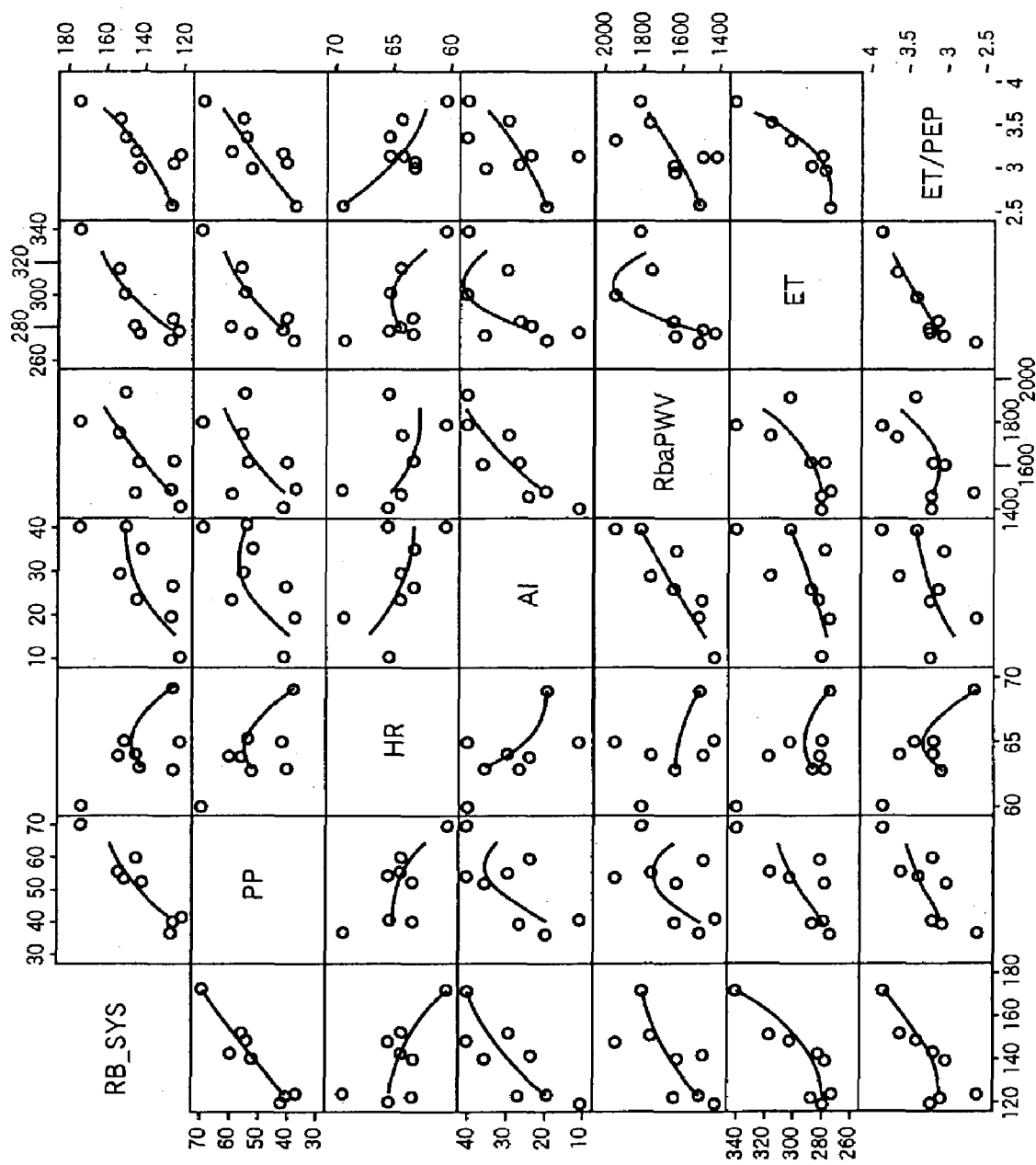
FIG. 9 is a graph showing scatter diagrams representing respective relationships between each one of the physical parameters shown in FIG. 8 and each of the other physical parameters.

Each of Expression 2 and Expression 3 has five parameters, and respective coefficients of those five parameters are experimentally determined for each individual patient. The reason why those expressions are used are as follows: FIG. 8 shows respective timewise changes of a plurality of physical parameters that are non-invasively obtained in half a year from a male person in his sixties who has been treated against hypertension, that is, respective timewise changes of pulse-wave velocity PWV, augmentation index AI, systolic blood pressure SYS, pulse pressure PP, pre-ejection period PEP, and ejection time ET. FIG. 9 shows scatter diagrams representing respective relationships between each one of the physical parameters shown in FIG. 8 and each of the other physical parameters. However, it is very difficult to judge, from the graphs shown in FIGS. 8 and 9, the effect of antihypertensive drug or treatment applied to the patient. Hereinafter, there will be described the technique of multivariate analysis as applied to the data shown in FIG. 8.

Figure 10:
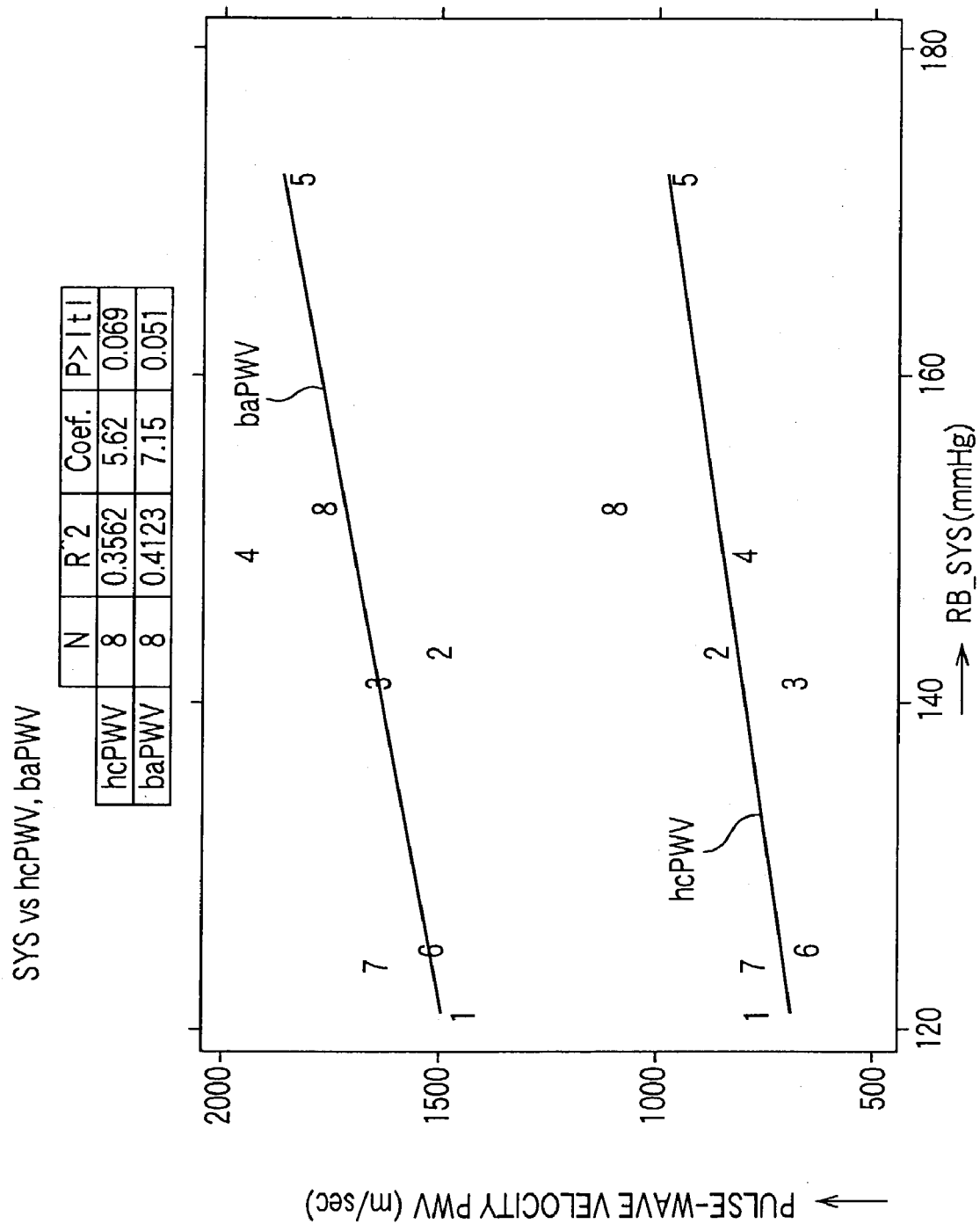
FIG. 10 is a graph showing a regression line calculated based on the data shown in FIG. 8 so as to determine a relationship between systolic (highest) blood pressure SYS and heart-to-carotid-artery pulse-wave velocity hcPWV, and a regression line calculated based on the data shown in FIG. 8 so as to determine a relationship between systolic blood pressure SYS and brachium-and-ankle pulse-wave velocity baPWV.
Figure 11:
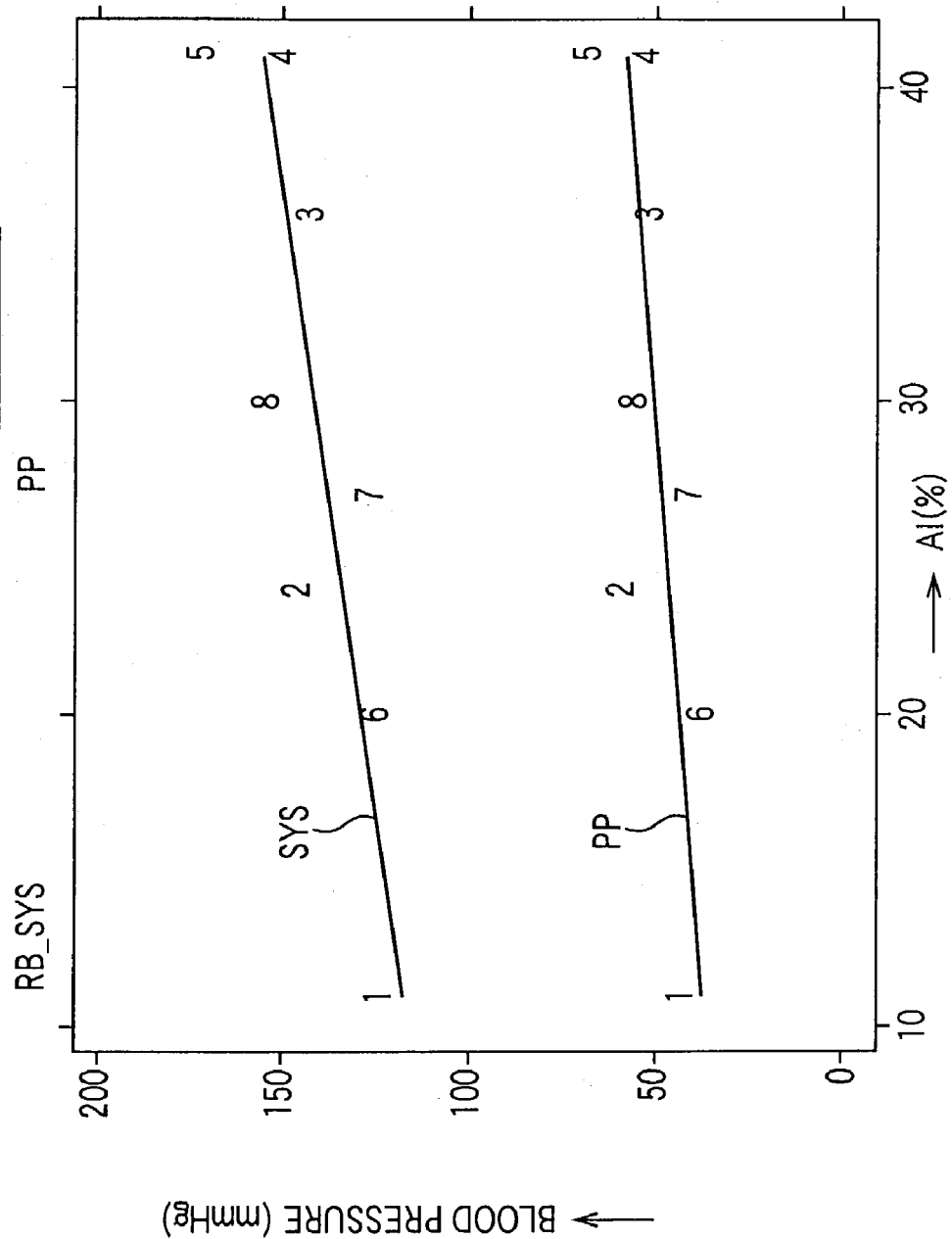
FIG. 11 is a graph showing a regression line calculated based on the data shown in FIG. 8 so as to determine a relationship between augmentation index AI and systolic blood pressure SYS, and a regression line calculated based on the data shown in FIG. 8 so as to determine a relationship between augmentation index AI and pulse pressure PP.
Figure 12:
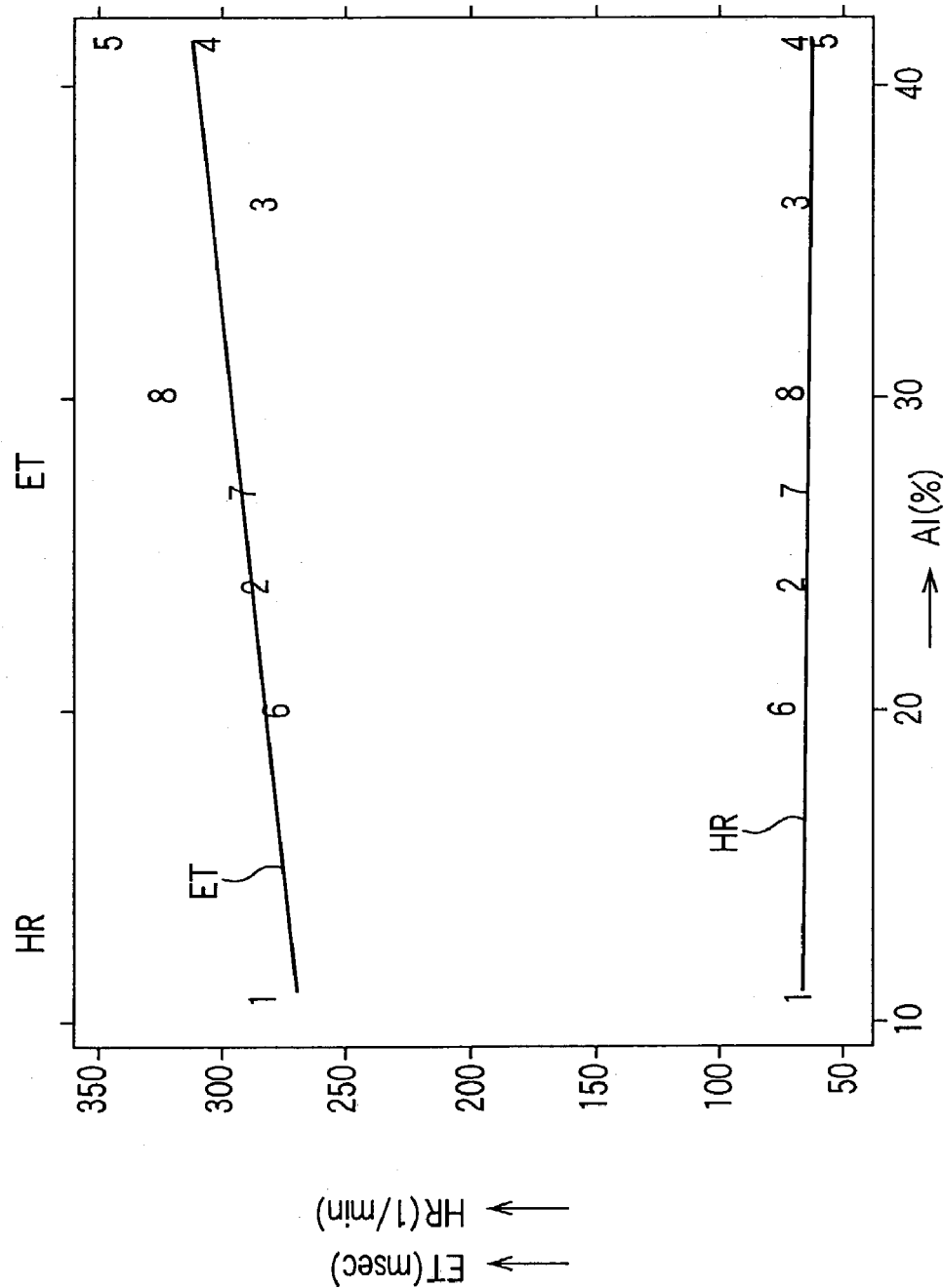
FIG. 12 is a graph showing a regression line calculated based on the data shown in FIG. 8 so as to determine a relationship between augmentation index AI and heart rate HR, and a regression line calculated based on the data shown in FIG. 8 so as to determine a relationship between augmentation index AI and ejection time ET.
Figure 13:
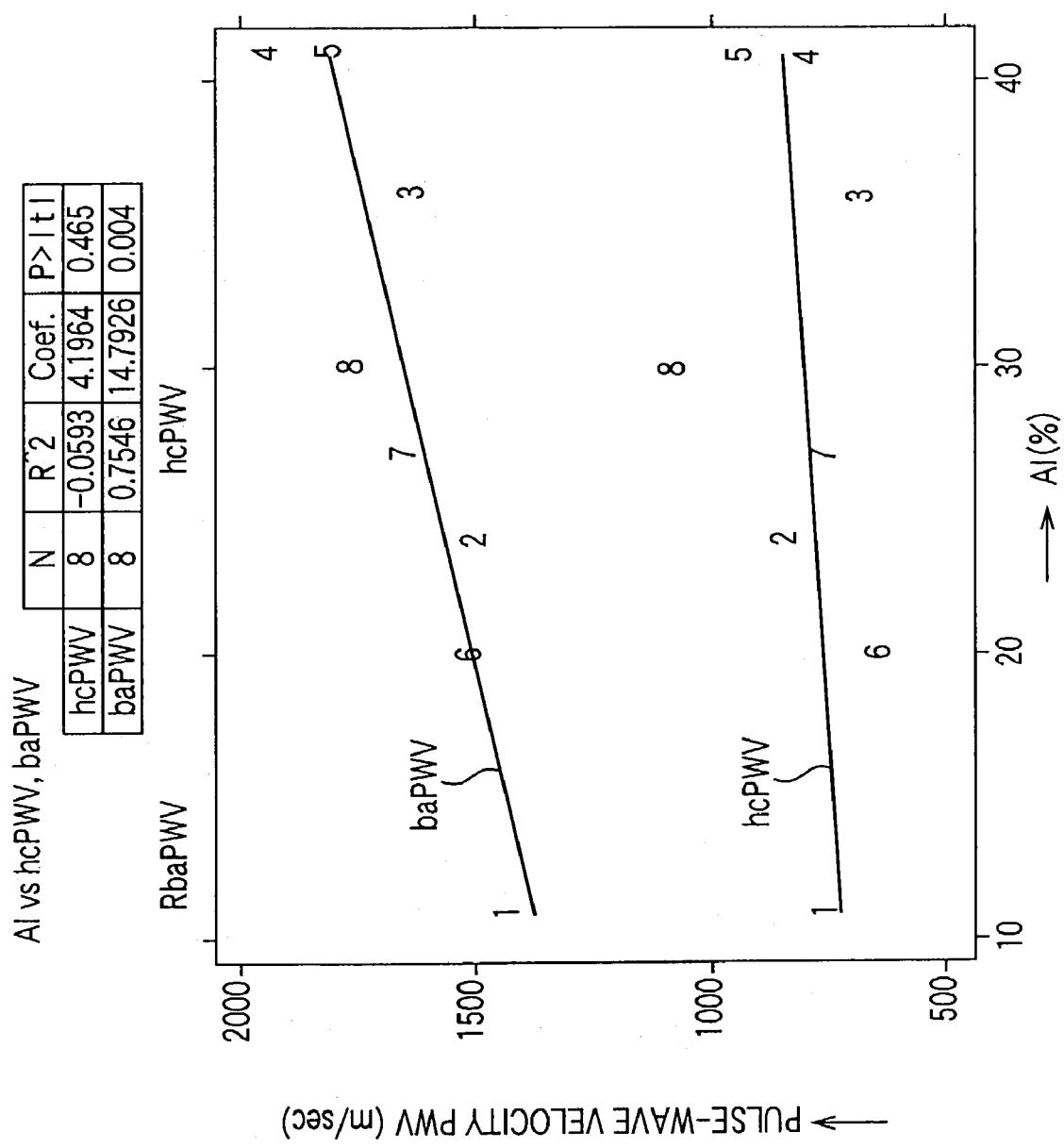
FIG. 13 is a graph showing a regression line calculated based on the data shown in FIG. 8 so as to determine a relationship between augmentation index AI and heart-to-carotid-artery pulse-wave velocity hcPWV, and a regression line calculated based on the data shown in FIG. 8 so as to determine a relationship between augmentation index AI and brachium-and-ankle pulse-wave velocity baPWV.

FIG. 10 is a graph showing a regression line calculated based on the data shown in FIG. 8 so as to determine a relationship between systolic (highest) blood pressure SYS and heart- and-carotid-artery pulse-wave velocity hcPWV (indicated in a lower half portion of FIG. 10), and a regression line calculated based on the data shown in FIG. 8 so as to determine a relationship between systolic blood pressure SYS and brachium-and-ankle pulse-wave velocity baPWV (indicated in an upper half portion of FIG. 10). From this graph, it is understood that there is a positive correlation between systolic blood pressure SYS and pulse-wave velocity PWV, but that the positive correlation is a significant tendency is the only judgment that can be made. FIG. 11 is a graph showing a regression line calculated based on the data shown in FIG. 8 so as to determine a relationship between augmentation index AI and systolic blood pressure SYS (indicated in an upper half portion of FIG. 11), and a regression line calculated based on the data shown in FIG. 8 so as to determine a relationship between augmentation index AI and pulse pressure PP (unit: mmHg) (indicated in a lower half portion of FIG. 11). From this graph, it is understood that there is a positive correlation between augmentation index AI and systolic blood pressure SYS or pulse pressure PP, and it can be judged that the correlation between augmentation index AI and systolic blood pressure SYS is significant. FIG. 12 is a graph showing a regression line calculated based on the data shown in FIG. 8 so as to determine a relationship between augmentation index AI and heart rate HR (indicated in a lower half portion of FIG. 12), and a regression line calculated based on the data shown in FIG. 8 so as to determine a relationship between augmentation index AI and ejection time ET (indicated in an upper half portion of FIG. 12). From this graph, nothing can be understood about the relationship between augmentation index AI and heart rate HR or ejection time ET. FIG. 13 is a graph showing a regression line calculated based on the data shown in FIG. 8 so as to determine a relationship between augmentation index AI and heart-and-carotid-artery pulse-wave velocity hcPWV (indicated in a lower half portion of FIG. 13), and a regression line calculated based on the data shown in FIG. 8 so as to determine a relationship between augmentation index AI and brachium-and-ankle pulse-wave velocity baPWV (indicated in an upper half portion of FIG. 13). From this graph, it is understood that there is a positive correlation between augmentation index AI and pulse-wave velocity PWV, and it can be judged that the correlation between augmentation index AI and pulse-wave velocity PWV is significant. Numerals 1 to 8 used in FIGS. 10 to 13 indicate the order of measurement; however, since changes are not uniform, it is difficult to judge whether arteriosclerosis has advanced or has been cured. In FIGS. 10 to 14, N is a population parameter; $R^2$ is square of correlation coefficient; Coef is coefficient of regression line; and P is significant difference.

Figure 14:
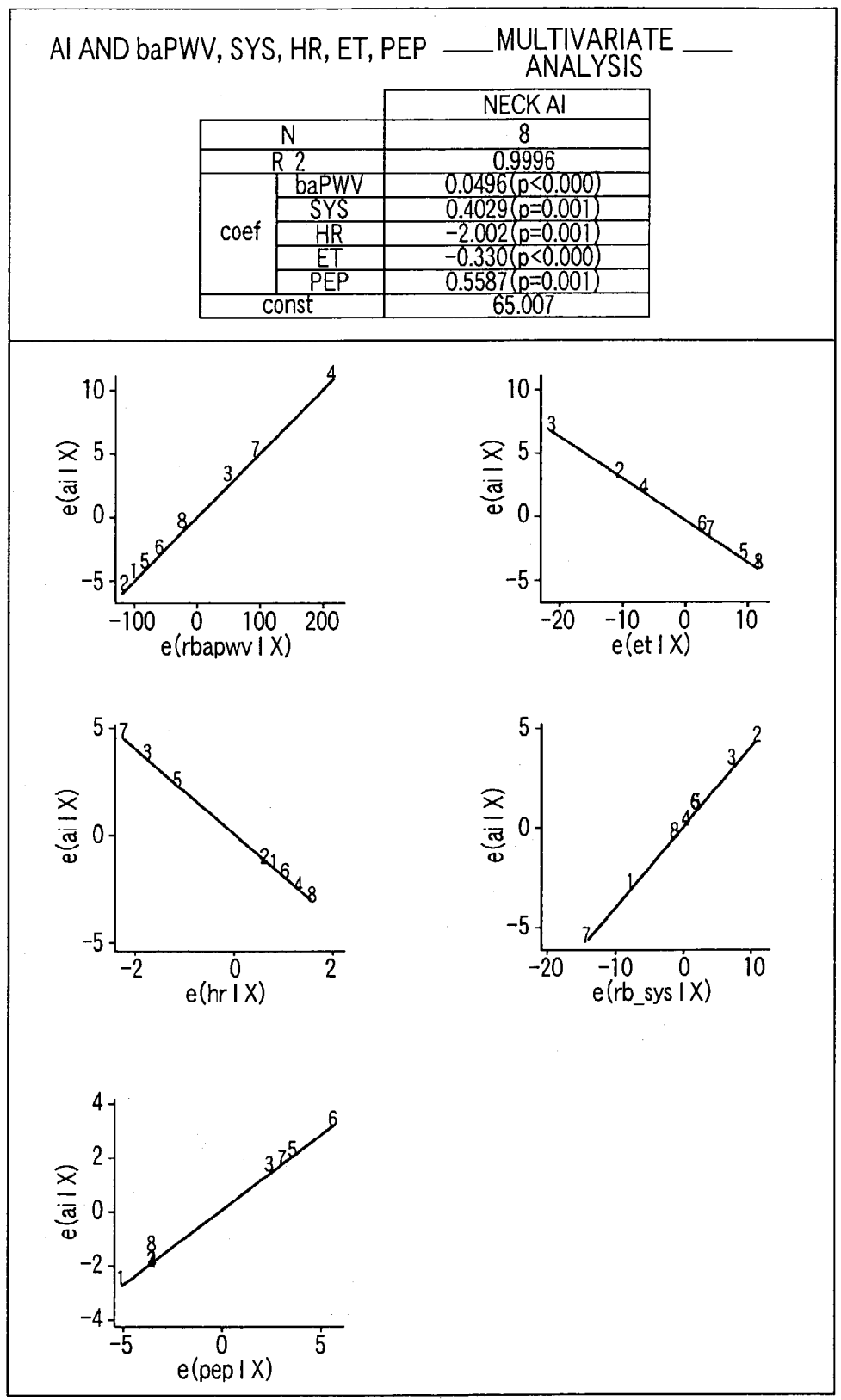
FIG. 14 is a view showing, regarding data shown in FIG. 8, respective coefficients of physical parameters, and a constant, of a right-hand side of a model (Expression 2) to which multivariate analysis is applied, and respective relationships between augmentation index $AI_E$ as a left-hand side of the model expression and the respective physical parameters of the right-hand side of the same.

FIG. 14 shows respective coefficients of physical parameters, and a constant, of a right-hand side of a model (e.g., Expression 2) to which multivariate analysis is applied, and respective relationships between augmentation index $AI_E$ as a left-hand side of the model expression and the respective physical parameters of the right-hand side of the same. The coefficients and constant and the relationships are obtained from the data shown in FIG. 8. A sufficiently high degree of correlation is obtained by the model shown in FIG. 14. This model defines a relationship between arteriosclerosis-inspection-related augmentation index $AI_E$, and pulse-wave velocity PWV, systolic blood pressure SYS, heart rate HR, ejection time ET, and pre-ejection period PEP. More specifically described, augmentation index AI or pulse-wave velocity PWV is a parameter indicative of the compliance of blood vessels. However, since each parameter AI, PWV depends on blood pressure, activity of autonomic nerve, cardiac output, and preload and transient load, it cannot be said that the each parameter accurately indicates the condition of circulatory organ. To avoid this problem, the above-indicated model has incorporated systolic blood pressure SYS as explanatory variable (i.e., blood-pressure-related factor) indicative of the influence of blood pressure, heart rate HR as explanatory variable (i.e., autonomic-nerve-related factor) indicative of the influence of activity of autonomic nerve; ejection time ET as explanatory variable (i.e., cardiac-output-related factor) indicative of the influence of cardiac output; and pre-ejection period PEP as explanatory variable (i.e., preload-and-transient-load-related factor) indicative of the influence of preload and transient load. That is, this model employs the largest possible number of essential factors related to the condition of circulatory organ. Therefore, an accurate augmentation index AI can be obtained and it can be used for inspection of arteriosclerosis. Thus, the effect of drug or treatment against arteriosclerosis can be accurately judged or evaluated. Expression 4, indicated below, is derived from Expression 2 by applying multivariate analysis to the data shown in FIG. 8. If an index AI estimated according to Expression 4 is equal to an actually measured AI, then it can be readily judged that there is no change in arteriosclerosis.

Figure 15:
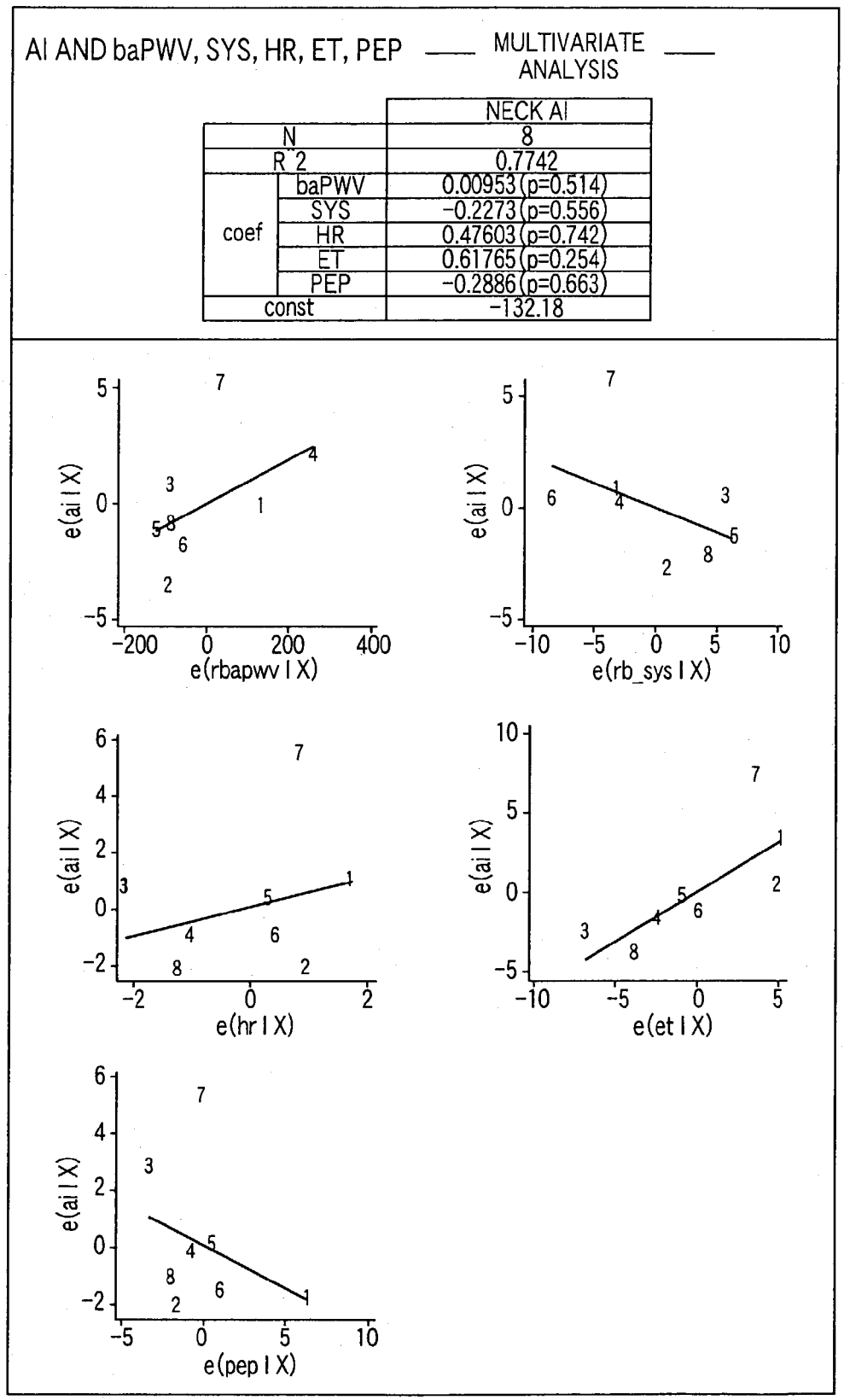
FIG. 15 is a view showing, regarding data obtained in a year from a male person in his fifties who has been treated against hypertension, respective coefficients of physical parameters, and a constant, of a right-hand side of a model (Expression 2) to which multivariate analysis is applied, and respective relationships between augmentation index $AI_E$ as a left-hand side of the model expression and the respective physical parameters of the right-hand side of the same.

FIG. 15 shows, regarding data obtained in a year from a male person in his fifties who has been treated against hypertension, respective coefficients of physical parameters, and a constant, of a right-hand side of a model (e.g., Expression 2) to which multivariate analysis is applied, and respective relationships between augmentation index $AI_E$ as a left-hand side of the model expression and the respective physical parameters of the right-hand side of the same. Expression 5, indicated below, is derived from Expression 2 by applying multivariate analysis to the data shown in FIG. 8. According to this expression, the operator can judge whether antihypertensive drugs or treatments have been changed during the above-indicated term, or, whether arteriosclerosis has changed because of treatment. More specifically described, based on the coefficient of each of the parameters of the expression and the measured value of the each parameter, the operator can judge whether arteriosclerosis has been improved by the effect of treatment, or not, and how the condition of circulatory organ of the subject has changed. For example, in the case where pulse-wave velocity PWV is changed by changing of blood pressure, the coefficient of the parameter in Expression 5 indicates the compliance of blood vessels that includes the influence to the condition of circulatory organ. If each of the coefficients changes because of each sort of treatment, a person can judge the effect of the each treatment. In FIGS. 14 and 15, e (parameter|X) on each of vertical and horizontal axes of each two-dimensional graph represents a relationship between a parameter on horizontal axis and a target variable on vertical axis, that is free from the influences of the other explanatory variables.

$$AI_E = 0.0496PWV + 0.4029SYS - 2.2002HR - 0.330ET + 0.5587PEP + 65.007 \quad (4)$$

$$PWV_E = 0.00953AI - 0.2273SYS + 0.47603HR + 0.61765ET - 0.2886PEP - 132.18 \quad (5)$$

Like the above-described arteriosclerosis-inspection-related augmentation index $AI_E$, an arteriosclerosis-inspection-related pulse-wave velocity $PWV_E$ is determined, for each individual patient, according to an expression that is derived in advance from Expression 3 by applying multivariate analysis to data obtained from the each patient. The thus determined velocity can be used to make a diagnosis or select a treatment.

Therefore, if a difference the arteriosclerosis-inspection-related augmentation index $AI_E$, determined according to Expression 2 and displayed by the display device 79, from a reference index determined at a reference time (e.g., a certain time before administration of a drug) falls in a 95% confidence interval, then it can be judged that there is no effect of treatment; and if the difference is greater than the interval, then the respective coefficients and constant of the expression are re-determined, and whether there is any effect of treatment or how the condition of circulatory organ has changed, can be judged based on the re-determined coefficients and constant and/or respective changes of the re-determined coefficients and constant from the previous coefficients and constant. Likewise, if a difference the arteriosclerosis-inspection-related pulse-wave velocity $PWV_E$, determined according to Expression 3 and displayed by the display device 79, from a reference index determined at a reference time (e.g., a certain time before administration of a drug) falls in a 95% confidence interval, then it can be judged that there is no effect of treatment; and if the difference is greater than the interval, then the respective coefficients and constant of the expression are re-determined, and whether there is any effect of treatment or how the condition of circulatory organ has changed, can be judged based on the re-determined coefficients and constant and/or respective changes of the re-determined coefficients and constant from the previous coefficients and constant.

Figure 16:
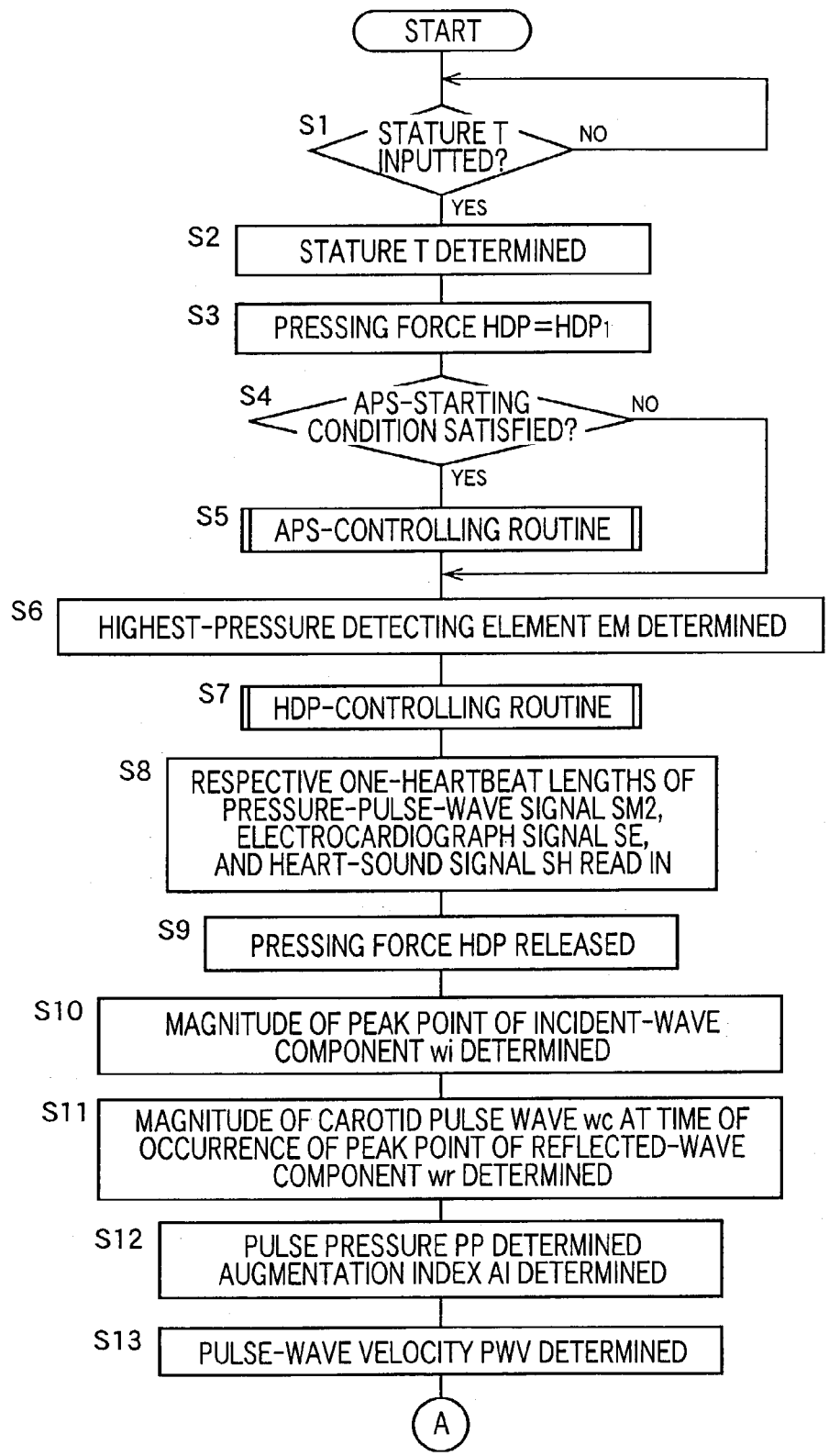
FIG. 16 is a view showing a first half portion of a flow chart representing the control functions of a CPU (central processing unit) of the control device, shown in FIG. 6.
Figure 17:
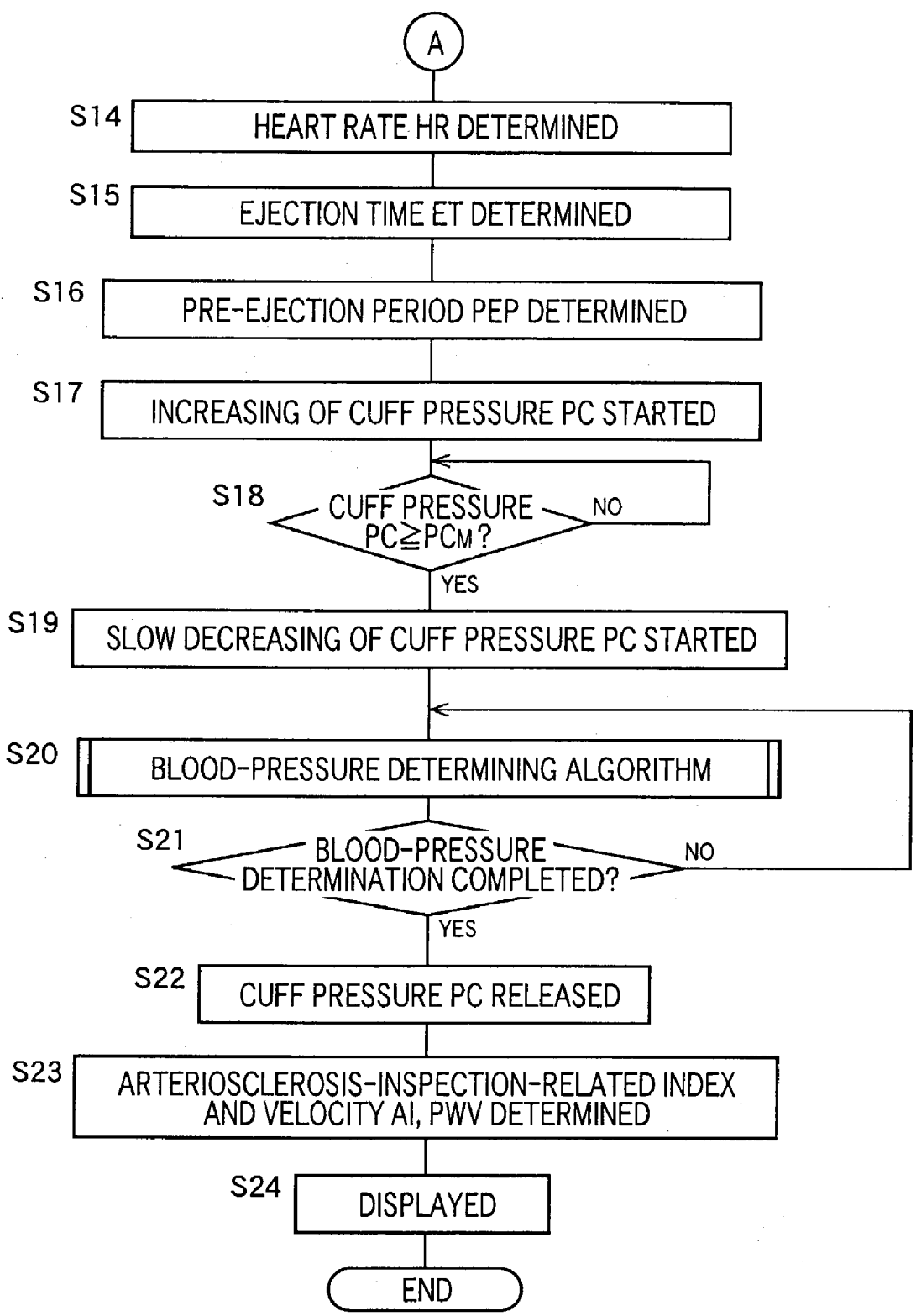
FIG. 17 is a view showing a second half portion of the flow chart representing the control functions of the CPU, shown in FIG. 6.

FIGS. 16 and 17 are a flow chart representing the control functions of the CPU 76 of the electronic control device 32, shown in the diagrammatic view of FIG. 6.

In FIG. 16, first, the CPU carries out Step S1 (hereinafter, each term "Step(s)" is omitted). At S1, the CPU judges whether the input device 72 has been operated to input a stature T of a living subject, i.e., whether the CPU has received a stature signal ST from the input device 72. S1 is repeated until a positive judgment is made. Meanwhile, if a positive judgment is made at S1, the control goes to S2 corresponding to the stature determining means 94. At S2, the CPU determines or identifies a stature T of the subject based on the stature signal ST supplied from the input device 72.

Then, the control goes to S3 to S5 corresponding to the optimum-pressing-position determining means 80. First, at S3, the CPU operates the pressing device 62 to change the pressure in the pressure chamber 56 and thereby change the pressing force HDP applied to the pressure-pulse-wave sensor 54, to a pre-set first pressing force HDP1. This first pressing force HDP1 is experimentally determined, in advance, as a pressing force HDP that assures that respective S/N ratios of respective carotid pulse waves wc detected by the respective pressure-sensing elements E are so great as to be able to determine respective magnitudes of respective peak points pc of those carotid pulse waves wc.

Then, at S4, the CPU judges whether a pressing-position updating condition (i.e., an APS starting condition) has been satisfied, e.g., whether one EM of the pressure-sensing elements E provided in the press surface 66 of the sensor 54 that detects the highest one of the respective pressures detected by all the elements E is located in one of prescribed opposite end portions of the array of elements E. If a negative judgment is made at S3, the control goes to S6, described later.

On the other hand, if a positive judgment is made at S4, i.e., if a current position of the pressure-pulse-wave sensor 54 relative to the carotid artery 46 is not appropriate, the control goes to S5 to perform an APS-controlling routine. In this routine, the CPU operates for moving the sensor 54 to an optimum pressing position where the highest-pressure detecting element EM is located at substantially the middle of the array of elements E. More specifically, first, the CPU operates the pressing device 62 to once move the sensor 54 off the body surface 50, subsequently operates the widthwise-direction moving device 64 to move the pressing device 62 and the sensor 54 over a predetermined distance, and then operates the pressing device 62 to press again the sensor 54 at the first pressing force HDP1. In this state, the CPU judges whether the highest-pressure detecting element EM is located in a prescribed middle range of the array of pressure-sensing elements E. The above-described pressing and judging operations are repeated until a positive judgment is made.

If at S5 the pressure-pulse-wave sensor 54 is positioned at the optimum pressing position, or if a positive judgment is made at S4, the control goes to S6 to identify the highest-pressure detecting element EM in the current condition, and then to S7 corresponding to the pressing-force determining means 82, i.e., an HDP-controlling routine. More specifically described, the CPU operates the pressing device 62 so that the pressing force HDP applied to the sensor 54 is continuously increased from the first pressing force HDP1. During this increasing of the pressing force HDP, the CPU determines an optimum pressing force HDPO at which a pulse pressure PP of the carotid pulse wave wc detected by the highest-pressure detecting element EM, determined at S6, is greater than a pre-set lower-limit pulse pressure $PP_L$, and maintains the pressing force HDP applied to the sensor 54, at the thus determined optimum pressing force HDPO.

Then, the control goes to S8 where the CPU reads in the pressure-pulse-wave signal SM2 supplied from the highest-pressure detecting element EM of the pressure-pulse-wave sensor 54, the electrocardiogram signal SE supplied from the electrocardiograph 68, and the heart-sound signal SH supplied from the heart-sound microphone 70, during a time period between a time of detection of one R-wave represented by the signal SE and a time of detection of the next R-wave. Thus, the CPU reads in one heartbeat-synchronous pulse of each of the signal SM2, the signal SE, and the signal SH. Then, the control goes to S9 to stop the air pump 58 and operate the pressure control valve 60 so that the pressing force HDP applied to the sensor 54 is decreased to an atmospheric pressure.

Next, the control goes to S10 to S13 corresponding to the augmentation-index determining means 96. At S10, the CPU subjects, to a fourth-order differentiation treatment or analysis, a portion of the one heartbeat-synchronous pulse of the carotid pulse wave wc, read in at S8, that continues from a time corresponding to a rising point of the one pulse and to a time corresponding to a peak point pc of the same pulse, and thereby determines an inflection point or a maximal point occurring to the portion between the rising point and the peak point pc, and then determines a magnitude of the thus determined inflection or maximal point as a magnitude of a peak point pi of an incident wave wi.

Then, the control goes to S11 where the CPU determines a time of occurrence of a peak point of a reflected wave wr of the one pulse of the carotid pulse wave wc read in at S8, and determines a magnitude of the carotid pulse wave wc at the thus determined time of occurrence of the peak point of the reflected wave wr. More specifically described, if the magnitude of the peak point pi of the incident wave wi determined at S10 does not coincide with the greatest magnitude of the observed carotid pulse wave wc, a magnitude of the carotid pulse wave wc at a time of occurrence of the greatest magnitude of the carotid pulse wave wc is determined as a magnitude of the carotid pulse wave wc at the time of occurrence of the peak point of the reflected wave wr; and if the magnitude of the peak point pi of the incident wave wi coincides with the greatest magnitude of the observed carotid pulse wave wc, a magnitude of the carotid pulse wave wc at a time of occurrence of the first maximal magnitude following the peak point pi of the incident wave wi is determined as a magnitude of the carotid pulse wave wc at the time of occurrence of the peak point of the reflected wave wr.

Then, at S12 corresponding to the augmentation-index determining means 96, the CPU determines a pulse pressure PP of the one pulse of the carotid pulse wave wc read at S8. Subsequently, at S13, the CPU determines a pressure difference ΔP by subtracting the magnitude of the peak point pi of the incident wave wi, determined at S10, from the magnitude of the carotid pulse wave wc at the time of occurrence of the peak point of the reflected wave wr, determined at S11. The CPU substitutes, for the augmentation-index calculating formula represented by Expression 1, the thus determined pressure difference ΔP, and the pulse pressure PP determined at S12, so as to determine an augmentation index AI (%). Then, the control goes to S13 corresponding to the pulse-wave-velocity-related-information obtaining means 98. At S13, the CPU determines, as a propagation time DT, a delay time from the second heart sound II of the heart sounds detected by the heart-sound microphone 70, to the dichrotic notch of the carotid pulse wave detected by the pressure-pulse-wave sensor 54, and additionally determines a pulse-wave velocity PWV (=DL/DT) by dividing the pre-set distance DL that has been corrected by the stature T, by the propagation time DT. The second heart sound II corresponds to the closing of the aortic valve of the subject.

Next, there will be described S14 and the following steps shown in FIG. 17. First, at S14 corresponding to the heart-rate determining means 88, the CPU determines a pulse period RR equal to a time interval between respective R-waves of two successive heartbeat-synchronous pulses of the electrocardiogram signal SE read in at S8, and calculates a heart rate HR (/minute) by multiplying the inverse (1/RR) of the pulse period RR by 60.

Then, the control goes to S15 corresponding to the ejection-time determining means 90. At S15, the CPU determines a rising point and a dicrotic notch of the one heartbeat-synchronous pulse of the carotid pulse wave wc read in at S8, and determines, as an ejection time ET, a time difference between respective times of occurrence of the rising point and the dicrotic notch.

Subsequently, the control goes to S16 corresponding to the pre-ejection-period determining means 92. At S16, the CPU determines a start point of a second heart sound II of the heart-sound waveform (i.e., phonocardiogram) read in at S8, determines a time period T1 from a time of occurrence of an R-wave of the electrocardiogram to a time of occurrence of the start point of the second heart sound II, and finally determines a pre-ejection period PEP by subtracting, from the time period T1, the ejection time ET determined at S15.

Then, the control goes to S17 to S22 to measure blood-pressure values BP of the subject. First, at S17, the CPU starts the air pump 24 and operate the pressure control valve 18 so as to start quickly increasing the cuff pressure PC. Subsequently, at S18, the CPU judges whether the cuff pressure PC has exceeded an increase-target pressure $PC_M$ pre-set at 180 mmHg. S18 is repeated until a positive judgment is made, while the cuff pressure PC is quickly increased. Meanwhile, if a positive judgment is made at S18, the control goes to S19 to stop the air pump 24 and operate the pressure control valve 18 so as to start slowly decreasing the cuff pressure PC at a rate of about 3 mmHg/sec.

Next, the control goes to S20 and S21 corresponding to the blood-pressure determining means 86. At S20, the CPU determines, based on change of respective amplitudes of successive heartbeat-synchronous pulses of the upper-arm pulse wave represented by the cuff-pulse-wave signal SM1 continuously obtained during the slow decreasing of the cuff pressure PC, a systolic blood pressure $BP_{SYS}$, a mean blood pressure $BP_{MEAN}$, and a diastolic blood pressure $BP_{DIA}$ of the subject, according to well-known oscillometric blood-pressure determining algorithm. Then, at S21, the CPU judges whether the determination of the blood-pressure values BP has completed at S20. Since the diastolic blood pressure $BP_{DIA}$ is last determined at S20, the CPU judges, at S21, whether the diastolic blood pressure $BP_{DIA}$ has been determined. S20 is repeated until a positive judgment is made at S21, while the blood-pressure determining algorithm is continued.

Meanwhile, if a positive judgment is made at S21, the control goes to S22 corresponding to the arteriosclerosis-inspection-related-parameter-value determining means 100. At S22, the CPU determines an arteriosclerosis-inspection-related augmentation index $AI_E$ of the subject based on the pulse-wave-velocity-related information, e.g. pulse-wave velocity PWV, obtained by the pulse-wave-velocity-related-information obtaining means 98, the blood pressure, e.g., systolic blood pressure SYS determined by the blood-pressure determining means 86 (S20), the heart rate HR determined by the heart-rate determining means 88, the pre-ejection period PWP determined by the pre-ejection-period determining means 92, and the ejection time determined by the ejection-time determining means 90, according to Expression 2 pre-stored in the ROM 77, and additionally determines an arteriosclerosis-inspection-related pulse-wave-velocity-related value, e.g., pulse-wave velocity $PWV_E$ of the subject, based on the augmentation index AI determined by the augmentation-index determining means 96, the blood pressure, e.g., systolic blood pressure SYS, determined by the blood-pressure determining means 86 (S20), the heart rate HR determined by the heart-rate determining means 88, the pre-ejection period PEP determined by the pre-ejection-period determining means 92, and the ejection time determined by the ejection-time determining means 90, according to Expression 3 pre-stored in the ROM 77.

Then, the control goes to S23 corresponding to the display control means 102. At S23, the CPU operates the display device 79 to display the arteriosclerosis-inspection-related augmentation index $AI_E$ and/or the arteriosclerosis-inspection-related pulse-wave velocity $PWV_E$, each determined at S22 corresponding to the arteriosclerosis-inspection-related-parameter-value determining means 100, in such a manner that the index $AI_E$ and/or the velocity PWVE are/is indicated in digital values such as numerals or in analog values such as bar graphs, so that the operator can easily make a diagnosis based on the indicated index and/or velocity. Simultaneously, the CPU operates the display device 79 to display Expression 2 and/or Expression 3, and the coefficients a, b, c, d, and e and the constant f of Expression 2 and/or the coefficients a', b', c', d', and e' and the constant f' of Expression 3. In addition, if the control device 32 has determined and stored, for the same patient, one or more past arteriosclerosis-inspection-related augmentation index values $AI_E$ and/or one or more past arteriosclerosis-inspection-related pulse-wave velocity values $PWV_E$, and one or more past sets of coefficients and constant of Expression 2 and/or Expression 3, then the CPU operates the display device 79 to display respective data points of each of those parameters along a time axis, or respective differences of the respective data points of each parameter from their previous data points, so that the operator can easily observe respective time-wise changes of those parameters.

As is apparent from the foregoing description of the present embodiment, the arteriosclerosis-inspection-related-parameter-value determining means 100 (S23) determines the arteriosclerosis-inspection-related augmentation index $AI_E$ as a sort of arteriosclerosis-inspection-related parameter, based on the pulse-wave velocity PWV (pulse-wave-velocity-related information) obtained by the pulse-wave-velocity-related-information obtaining means 98 (S13), the blood pressure BP (SYS) determined by the blood-pressure determining means 86 (S20), the heart rate HR determined by the heart-rate determining means 88 (S14), the pre-ejection period PEP determined by the pre-ejection-period determining means 92 (S16), and the ejection time ET determined by the ejection-time determining means 90 (S15), according to the pre-stored Expression 2. Thus, the arteriosclerosis-inspection-related augmentation index $AI_E$ is determined based on the pulse-wave velocity corresponding to the elasticity of blood vessels of the subject, the blood pressure BP (SYS) of the subject, the heart rate HR corresponding to the activity of autonomic nerve of the subject, and the pre-ejection period PEP and the ejection time ET both corresponding to the cardiac (e.g., cardiac-output) function of the subject. Therefore, the arteriosclerosis-inspection-related augmentation index enjoys a high degree of reliability reflecting the condition of circulatory organ of the subject and can be used to make an accurate diagnosis on arteriosclerosis of the subject. Thus, the accuracy of diagnosis of arteriosclerosis is improved.

In addition, in the present embodiment, the arteriosclerosis-inspection-related-parameter-value determining means 100 (S23) determines the arteriosclerosis-inspection-related pulse-wave velocity $PWV_E$ based on the augmentation index AI determined by the augmentation-index determining means 96 (S12), the blood pressure BP (SYS) determined by the blood-pressure determining means 86 (S20), the heart rate HR determined by the heart-rate determining means 88 (S14), the pre-ejection period PEP determined by the pre-ejection-period determining means 92 (S16), and the ejection time ET determined by the ejection-time determining means 90 (S15), according to the pre-stored Expression 2. Thus, the arteriosclerosis-inspection-related pulse-wave velocity $PWV_E$ is determined based on the augmentation index AI corresponding to the elasticity of blood vessels of the subject, the blood pressure BP (SYS) of the subject, the heart rate HR corresponding to the activity of autonomic nerve of the subject, and the pre-ejection period PEP and the ejection time ET both corresponding to the cardiac (e.g., cardiac-output) function of the subject. Therefore, the arteriosclerosis-inspection-related pulse-wave velocity enjoys a high degree of reliability reflecting the condition of circulatory organ of the subject and can be used to make an accurate diagnosis on arteriosclerosis of the subject. Thus, the accuracy of diagnosis of arteriosclerosis is improved.

In addition, in the present embodiment, the display device 79 displays the coefficients a, b, c, d, and e and the constant f of the expression according to which the arteriosclerosis-inspection-related augmentation index $AI_E$ is determined, and/or the coefficients a', b', c', d', and e' and the constant f' of the expression according to which the arteriosclerosis-inspection-related pulse-wave velocity $PWV_E$ is determined. The above coefficients and constants are determined in advance for each individual patient. In addition, the display device 79 may display the respective changes of the coefficients and constants. Therefore, the operator can accurately evaluate the effect of antihypertensive treatment.

While the present invention has been described in its preferred embodiment by reference to the drawings, it is to be understood that the invention may otherwise be embodied.

For example, in the illustrated arteriosclerosis inspecting apparatus 10, the pressure-pulse-wave detecting probe 36 for detecting the carotid pulse wave wc is employed as the pulse-wave detecting device. However, the pulse-wave detecting device may be one which detects a pulse wave from a different portion than the neck portion 38; such as an upper arm, a wrist, a femoral portion, or an ankle of the subject.

Generally, the denominator of the augmentation-index calculating formula (Expression 1) employed in the illustrated embodiment to determine the augmentation index AI is the pulse pressure PP. However, the pulse pressure PP of Expression 1 may be replaced with the amplitude (i.e., the magnitude) of the carotid pulse wave wc at the time of occurrence of the peak point of the incident-wave component thereof, because the formula employing the amplitude as the denominator indicates arteriosclerosis.

In the illustrated embodiment, pulse-wave velocity PWV is employed as the pulse-wave-velocity-related information or value. However, pulse-wave propagation time DT corresponding, one to one, to pulse-wave velocity PWV may be employed as the pulse-wave-velocity-related information or value. In addition, in the illustrated embodiment, pulse-wave velocity PWV is determined based on a time difference between the time of occurrence of second heart sound II and the time of occurrence of dicrotic notch of carotid pulse wave. However, pulse-wave velocity may be determined based on a time difference between respective pulse waves detected by two pulse-wave sensors from different portions of the subject, for example, brachial artery and ankle artery.

In the illustrated embodiment, heart rate HR is determined based on the waveform of the electrocardiogram. However, heart rate can be determined based on pulsation of the subject. In addition, in the illustrated embodiment, systolic blood pressure SYS is employed as the blood pressure. However, mean blood pressure or diastolic blood pressure may be used as the blood pressure of the subject.

In the illustrated embodiment, pre-ejection period PEP is calculated by subtracting the ejection time ET between the rising point, and dicrotic notch, of the carotid pulse wave, from the time T1 between the time of detection of R-wave of the electrocardiogram and the time of detection of starting point of second heart sound II contained in the heart sounds detected by the heart-sound microphone 70. However, pre-ejection period PEP and ejection time ET may be determined in different manners. For example, pre-ejection period PEP may be determined based on a time difference between the R-wave and the first heart sound I, and ejection time ET may be determined by subtracting the pre-ejection period PEP from the time T1.

The present invention may be embodied with other various changes without departing from the spirit of the invention.

What is claimed is:

1. An apparatus for inspecting arteriosclerosis of a living subject, comprising:
   a pulse-wave-velocity-related-information obtaining device which obtains pulse-wave-velocity-related information that is related to a velocity at which a pulse wave propagates in the subject;
   a blood-pressure measuring device which measures a blood pressure of the subject;
   a heart-rate measuring device which measures a heart rate of the subject;
   a pre-ejection-period measuring device which measures a pre-ejection period from a time of starting of contraction of the heart of the subject to a time of starting of ejection of blood from the heart;
   an ejection-time measuring device which measures an ejection time from the time of starting of ejection of blood from the heart to a time of ending of ejection of blood from the heart; and
   an arteriosclerosis-inspection-related-augmentation-index determining means for determining an arteriosclerosis-inspection-related augmentation index of the subject, based on the pulse-wave-velocity-related information obtained by the pulse-wave-velocity-related-information obtaining device, the blood pressure measured by the blood-pressure measuring device, the heart rate measured by the heart-rate measuring device, the pre-ejection period measured by the pre-ejection-period measuring device, and the ejection time measured by the ejection-time measuring device, according to a predetermined relationship between (A) (a1) pulse-wave-velocity-related information, (a2) blood pressure, (a3) heart rate, (a4) pre-ejection period and (a5) ejection time, and (B) arteriosclerosis-inspection-related augmentation index.

2. An apparatus according to claim 1, wherein the predetermined relationship is represented by a following expression:

$$AI_E = a \times PWV + b \times BP + c \times HR + d \times ET + e \times PEP + f$$

where PWV is pulse-wave-velocity-related information,
BP is blood pressure,
HR is heart rate,
PEP is pre-ejection period
ET is ejection time,
$AI_E$ is arteriosclerosis-inspection-related augmentation index,
a, b, c, d, and e are coefficients, and
f is a constant.

3. An apparatus according to claim 1, further comprising a display device which displays the arteriosclerosis-inspection-related augmentation index of the subject determined by the arteriosclerosis-inspection-related-augmentation-index determining means.

4. An apparatus according to claim 2, wherein the predetermined relationship is predetermined for each living subject, and wherein the apparatus further comprises a display device which displays the coefficients a, b, c, d, and e and the constant f of the predetermined relationship.

5. An apparatus according to claim 1, further comprising a memory device which stores the predetermined relationship.

6. An apparatus for inspecting arteriosclerosis of a living subject, comprising:
   an augmentation-index measuring device which measures an augmentation index of the subject that is a proportion of a magnitude of a reflected-wave component of a pulse wave of the subject to a magnitude of an incident-wave component of the pulse wave;
   a blood-pressure measuring device which measures a blood pressure of the subject;
   a heart-rate measuring device which measures a heart rate of the subject;
   a pre-ejection-period measuring device which measures a pre-ejection period from a time of starting of contraction of the heart of the subject to a time of starting of ejection of blood from the heart;
   an ejection-time measuring device which measures an ejection time from the time of starting of ejection of blood from the heart to a time of ending of ejection of blood from the heart; and
   an arteriosclerosis-inspection-related-pulse-wave-velocity-related-value determining means for determining an arteriosclerosis-inspection-related pulse-wave-velocity-related value of the subject, based on the augmentation index measured by the augmentation-index measuring device, the blood pressure measured by the blood-pressure measuring device, the heart rate measured by the heart-rate measuring device, the pre-ejection period measured by the pre-ejection-period measuring device, and the ejection time measured by the ejection-time measuring device, according to a predetermined relationship between (A) (a1) augmentation index, (a2) blood pressure, (a3) heart rate, (a4) pre-ejection period and (a5) ejection time, and (B) arteriosclerosis-inspection-related pulse-wave-velocity-related value.

7. An apparatus according to claim 6, wherein the predetermined relationship is represented by a following expression:

$$PWV_E = a' \times AI + b' \times BP + c' \times HR + d' \times ET + e' \times PEP + f'$$

where $PWV_E$ is arteriosclerosis-inspection-related pulse-wave-velocity-related value,
BP is blood pressure,
HR is heart rate,
PEP is pre-ejection period
ET is ejection time,
AI is augmentation index,
a', b', c', d', and e' are coefficients, and
f' is a constant.

8. An apparatus according to claim 6, further comprising a display device which displays the arteriosclerosis-inspection-related pulse-wave-velocity-related value of the subject determined by the arteriosclerosis-inspection-related-pulse-wave-velocity-related-value determining means.

9. An apparatus according to claim 7, wherein the predetermined relationship is predetermined for each living subject, and wherein the apparatus further comprises a display device which displays the coefficients a', b', c', d', and e' and the constant f' of the predetermined relationship.

10. An apparatus according to claim 6, further comprising a pulse-wave detecting device which detects the pulse wave from the subject.

* * * * *